US006410328B1

(12) United States Patent
Maclachlan et al.

(10) Patent No.: US 6,410,328 B1
(45) Date of Patent: Jun. 25, 2002

(54) SENSITIZING CELLS TO COMPOUNDS USING LIPID-MEDIATED GENE AND COMPOUND DELIVERY

(75) Inventors: Ian Maclachlan; Susan S. Buchkowsky; Roger W. Graham, all of Vancouver (CA)

(73) Assignee: Protiva Biotherapeutics Inc., Burnaby (CA)

(*) Notice: Subject to any disclaimer, the term of this patent is extended or adjusted under 35 U.S.C. 154(b) by 0 days.

(21) Appl. No.: 09/243,104

(22) Filed: Feb. 2, 1999

Related U.S. Application Data

(60) Provisional application No. 60/112,384, filed on Dec. 14, 1998, provisional application No. 60/073,598, filed on Feb. 3, 1998, provisional application No. 60/101,429, filed on Sep. 22, 1998, and provisional application No. 60/086,917, filed on May 27, 1998.

(51) Int. Cl.$^7$ ............................................... C12N 15/88
(52) U.S. Cl. ..................... 435/458; 514/44; 424/93.2; 435/320.1; 435/455
(58) Field of Search ............................. 435/320.1, 325, 435/455; 424/93.21, 450; 536/23.1; 514/44, 2

(56) References Cited

U.S. PATENT DOCUMENTS

| | | | |
|---|---|---|---|
| 5,459,127 A | * 10/1995 | Felgner | 514/7 |
| 5,543,152 A | 8/1996 | Webb et al. | 424/450 |
| 5,585,363 A | * 12/1996 | Scanlon et al. | 514/45 |
| 5,589,466 A | 12/1996 | Felgner et al. | 514/44 |
| 5,641,662 A | 6/1997 | Debs et al. | 435/455 |
| 5,676,954 A | 10/1997 | Brigham | 424/450 |
| 5,705,385 A | 1/1998 | Bally et al. | 435/320.1 |
| 5,753,613 A | 5/1998 | Ansell et al. | 514/2 |
| 5,827,831 A | * 10/1998 | Hostetler | 514/47 |
| 5,830,730 A | * 11/1998 | German | 435/455 |
| 5,962,424 A | * 10/1999 | Hallahan et al. | 514/44 |
| 6,083,530 A | * 7/2000 | Mayer et al. | 424/450 |
| 6,087,325 A | * 7/2000 | Meers et al. | 514/2 |
| 6,096,718 A | * 8/2000 | Weitzman | 514/44 |
| 6,110,490 A | * 8/2000 | Thierry | 424/450 |
| 6,214,388 B1 | * 4/2001 | Benz et al. | 424/812 |

FOREIGN PATENT DOCUMENTS

| | | |
|---|---|---|
| EP | 0 415 731 | 3/1991 |
| EP | 0 657 539 | 6/1995 |
| EP | 0 657 541 | 6/1995 |
| EP | 0 690 129 | 1/1996 |
| WO | WO 91/06309 | 5/1991 |
| WO | WO 93/12240 | 6/1993 |
| WO | WO 93/12756 | 7/1993 |
| WO | WO 93/24640 | 12/1993 |
| WO | WO 95/05835 | 3/1995 |
| WO | WO 96/03151 | 2/1996 |
| WO | WO 96/03515 | 2/1996 |
| WO | WO 96/16179 | 5/1996 |
| WO | WO 96/22277 | 7/1996 |
| WO | WO 96/39831 | 12/1996 |
| WO | WO 96/40964 | 12/1996 |
| WO | WO 97/07118 | 2/1997 |
| WO | WO 97/19180 | 5/1997 |
| WO | WO 97/19183 | 5/1997 |

OTHER PUBLICATIONS

Zerrouqi et al. Liposomal delivery fo the herpes simplex virus thymidine kinase gene in glioma: improvement of cell sensitization to ganciclovir. Cancer Gene Therapy, vol. 3, No. 6, 1996: pp. 385–392.*
Akoi, et al. Gene therapy for peritoneal dissemination of pancreatic cancer by liposome–mediated transfer of herpes simplex virus thymidine kinase gene. Human Gene Therapy 8: 1105–1113, 1997.*
Nishihara, et al. Retrovirus–mediated herpes simplex virus thymidine kinase gene transduction renders human thyroid carcinoma cell lines sensitive to ganciclovir and radiation in vitro and in vivo. Endocrinology, vol. 138, No. 11, pp. 4577–4583. 1997.*
Smith et al. Intracranial administration of adenovirus expressing HSV–TK in combination with ganciclovir produces a dose–dependent, self–limiting inflammatory response. Human Gene Therapy, 8: 943–954, 1997.*
Sasaki et al. Characterization of liposomes and an emulsion containing mitomycin C or lipophilic mitocycin C prodrugs. Journal of Pharmaceutical Sciences, vol. 75, No. 12, 1986, 1996.*
Rubas (Int. J. Cancer: 37, pp. 149–154, 1986.*
Bagshawe, Molecular Medicine Today, pp. 424–432, 1995.*
Dachs, Oncology Res., vol. 9, pp. 313–325, 1997.*
Mori et al, Pharmaceutical Res., vol. 10, 4, pp. 507–514, 1993.*
Tong et al., Acta Pharmaceutica Sinica, vol. 27, 1, pp. 15–21, 1991.*
Anderson, Nature, vol. 392, 25–30, 1998.*
Gupta et al., Enhancement of Therapeutic Effect of Cyclophosphamide Entrapped in Liposome in Walkers–256 Muscle Tumor of Rats, Dec. 1995, Biol. Mem., vol. 11, No. 2, pp. 146–151.*
Peyman et al., Intravitreal Injections of Liposome–Encapsulated Gancicovir in a Rabbit Model, 1987, Retina, vol. 7, No. 4, pp. 227–229.*
Mihailova et al., Liposome as Potential Pharmaceutical forms Effocacity of Cyclophosphamide Liposome By the Oral Route, Congr. Int. Technol. Pharm., 6$^{th}$ (1992), vol. 2, pp. 346–353.*
Gao et al., AN: 1987:605107, Caplus, 1987, vol. 22, No. 8.*
Alton, et al., *Nature Genetics*, 5:135–142 (1993).
Aoki, et al., *Hum. Gen. Ther.*, 8:1105–1113 (1997).
Black, et al., *PNAS (USA)*, 93:3525–3529 (1996).
Canonico, et al., *Am. J. Respir. Cell Mol. Biol.*, 10:24–29 (1994).

(List continued on next page.)

Primary Examiner—Dave T. Nguyen
(74) Attorney, Agent, or Firm—Townsend and Townsend and Crew, LLP

(57) ABSTRACT

The present invention relates to methods and compositions for sensitizing a cell to a prodrug compound.

22 Claims, 18 Drawing Sheets

OTHER PUBLICATIONS

Canonico, et al., *The American Physiological Society*, 415–419 (1994).
Caplen, et al., *Nature Medicine*, 1(1):39–46 (1995).
Hope, et al., *Biochim. et Biophys. Acta*, 812:55–65 (1985).
*Hum. Gene Ther.*, 7:255–267 (1996).
*Hum. Gene Ther.*, 8:597–613 (1997).
McLachlan, et al., *Gene Theapy.*, 3:1113–1123 (1996).
McLachlan, et al., *Gene Therapy*, 2:614–622 (1995).
Monnard, et al., *Biochim. et Biophys. Acta*, 1329:39–50 (1997).
Moolten, *Cancer Res.*, 46:5276–5281 (1986).
Nabel, et al., *Proc. Natl. Acad. Sci. USA*, 90:11307–11311 (1993).
Rubas, et al., *Int. J. Cancer*, 37:149–154 (1986).
Sikora, K., *OECD Documents, Gene Delivery Systems*, 59–71 (1996).
Stribling, et al., *PNAS*, 89:11277–11281 (1992).
Sugaya, et al., *Human Gen. Ther.*, 7:223–230 (1996).
Zerrouqui, et al., *Can. Gen. Therapy*, 3(6):385–392 (1996).
Database Medline, Accession No. 1998276748, 1998.

* cited by examiner

TUMOR MODEL

TUMOR SEEDING (I.D.)

5 DAYS (MCA 207)

TCS (I.V.)
GANCICLOVIR (I.P.)

MONITOR TUMOR GROWTH

TREATMENT REGIME

SENSITIZING CELLS TO COMPOUNDS USING LIPID-MEDIATED GENE AND COMPOUND DELIVERY

CROSS-REFERENCE TO RELATED APPLICATIONS

This application claims the benefit of U.S. Provisional patent application Ser. Nos. 60/112,384, filed Dec. 14, 1998, and 60/073,598, filed Feb. 3, 1998, which are incorporated herein by reference in their entirety for all purposes. This application is also related to U.S. patent application Ser. No. 09/243,102, filed Feb. 2, 1999 (Attorney Docket No. 016303-007320), which claims the benefit of U.S. Provisional Patent Application Ser. Nos. 60/101,429, filed Sep. 22, 1998 and 60/086,917, filed May 27, 1998, which are incorporated herein by reference in their entirety for all purposes.

FIELD OF THE INVENTION

This invention relates to methods and compositions for sensitizing a cell to a compound such as a prodrug.

BACKGROUND OF THE INVENTION

Working systems for in vivo human gene therapy are now established. Gene therapy vectors can be delivered to human cells in vivo by direct (local) injection or inhalation; by modified adenoviruses (reviewed in Englehardt, J. F. "Methods for Adenovirus-Mediated Gene Transfer to Airway Epithelium" Chapter 11 in Methods in Molecular Medicine, Gene Therapy Protocols, Ed. P. Robbins, 1997, Humana Press Inc., Totowa, N.J.); by retroviruses (Olsen, J. C., et al., "Methods for the Use of Retroviral Vectors for Transfer of the CFTR Gene to Airway Epithelium," Chapter 10, Ibid.); by cationic lipid-plasmid aggregates (Nabel, G. J., et al., "Methods for Liposome-Mediated Gene Transfer to Tumor Cells in Vivo," Chapter 21, Ibid.; Son, K., et al., "Cationic Liposome-Mediated Gene Transfer to Tumor Cells in Vitro and In Vivo," Chapter 23, Ibid.); or, simply, by delivery of naked DNA (see, U.S. Pat. No. 5,589,466 to Felgner, et al.).

Systemic delivery for in vivo gene therapy, i.e., delivery of the vector to a distal target cell via body systems such as the circulation, which is a less well explored avenue, has been achieved using lipid-plasmid particles such as those disclosed in published PCT patent application WO 96/40964, U.S. Pat. No. 5,705,385, and U.S. patent applications Ser. Nos. 08/485,458, 08/484,282, 08/660,025, 08/856,374, 60/063,473 and 09/169,573, filed Oct. 9, 1998, all of which are assigned to the assignee of the instant invention and incorporated herein by reference. This latter format provides a fully encapsulated lipid-plasmid particle that protects the vector from nuclease degradation in serum, is non-immunogenic, is small in size and has a prolonged circulation half-life.

A variation of the basic gene therapy technique that is useful for therapeutic treatment is gene-delivered enzyme prodrug therapy ("GDEPT"). GDEPT is also known as the "suicide gene/prodrug" system and was first developed by Moolten, F. L., Cancer Res. 46:5276–5281 (1986). In addition, for a detailed review of GDEPT, see, Moolten, F. L., Chapter 11 (1995), The Internet Book Of Gene Therapy, Cancer Therapeutics, Eds. Sobol, R. E., Scanlon, K. J., Appelton & Lange. In this method, a heterologous gene, encoding an enzyme that promotes the metabolism of a first compound, to which the cell is less sensitive (i.e., the "prodrug"), into a second compound to which is cell is more sensitive, is delivered to a cell. The cell takes up the gene and expresses it. Then the prodrug is delivered to the cell. The enzyme will process the prodrug into the second compound, and respond accordingly. A suitable system proposed by Moolten is the herpes simplex virus—thymidine kinase (HSV-TK) gene, and the prodrug ganciclovir. This method has recently been employed in work such as that of Zerrouqui, et al., Cancer. Gen. Therapy 3(6):385–392 (1996). Cationic lipid-nucleic aggregates were used for local delivery of the TK gene to mouse tumors in Sugaya, S., et al., Hum. Gen. Ther. 7:223–230 (1996). Human clinical trials using a GDEPT system employing viral vectors have been proposed (see, Hum. Gene Ther. 8:597–613 (1997) and Hum. Gen. Ther. 7:255–267 (1996)).

Patent applications relating to the GDEPT method have been published under the following numbers: WO 97/19180; WO 97/07118; WO 96/22277; WO 97/19183; WO 96/16179; WO 96/03515; WO 96/03515; WO 96/03151; EP 690129; EP 657541; EP 657539; WO 95/05835 and EP 415731.

Prior art methods suffer from many deficiencies. Firstly, the vector systems employed to date in GDEPT are designed for local delivery of the vector only. These systems are also highly immunogenic and hinder repeat dosing. This limits the range of applications for GDEPT. Secondly, non-specific toxicity of the prodrug can prohibit delivery of a satisfactory amount of the prodrug for effecting the transformed cell. In addition, prior art prodrug formulations are rapidly cleared from the blood, thereby requiring less desirable treatment modalities such as repeat injections or intravenous drip.

Another deficiency with the prior art methods is that even though researchers struggle to improve gene delivery systems, virtually no work has explored improvements in the prodrug delivery system, or the possible advantages of syncopating methods of delivering prodrugs and the vector. If the gene vector element is delivered in a format different from the prodrug element (i.e., adenovirus delivered vector versus free drug), the biodistribution of the elements is different, thus complicating dosage requirements and associated toxicities.

Clearly, there remains a need in the art for a method that solves the problem of targeting both elements of the suicide gene/prodrug system to the same organ, tumor or disease site of interest. It would be advantageous if this method could also reduce non-specific toxicities of the suicide gene/prodrug elements and extend their half-life in blood. The present invention fulfills these and other needs.

SUMMARY OF THE INVENTION

The present invention provides, inter alia, methods and compositions for sensitizing a cell to a compound, such as a prodrug. In one embodiment, the present invention provides a method of sensitizing a cell to a compound, the method comprising: (a) transfecting a cell with a vector comprising a gene sequence encoding a gene-product that promotes the processing, i.e., conversion, of a first compound (e.g., a prodrug) into a second compound; and (b) delivering to the cell the first compound in a lipid formulation; wherein the cell is more sensitive to the second compound than to the first compound.

In the above method, both the vector and the first compound can be delivered in lipid formulations which can be the same or different. The lipid formulations, whether used to deliver the vector or first compound (e.g., prodrug), can be prepared from a variety of lipids, lipid conjugates and additional compatible components known in the art. The lipid formulations can be prepared, for example, from sphingomyelin and cholesterol. Moreover, the lipid formulations can contain additional components which improve the properties or characteristics of the formulations, such as leakiness, longevity in circulation, reduced toxicity, encapsulation efficiency, etc. Such components include, for example, cationic lipids, ATTA-lipid conjugates, PEG-lipid conjugates, targeting agents, etc. Once prepared, the lipid formulations can be administered or delivered to the cell using a variety of techniques known to those of skill in the art. For instance, the lipid formulations can be delivered systemically, regionally or locally.

In a preferred embodiment, the vector is also delivered in a lipid formulation, such as a lipid-encapsulated formulation that is prepared for in vivo administration. In another preferred embodiment, the vector is a cationic lipid-vector aggregate or particle. The vector can be, for example, a modified adenovirus, modified retrovirus or naked DNA. The gene-product can be any product which promotes the processing, i.e., conversion, of a first compound (e.g., a prodrug) into a second compound to which the cell of interest is sensitive or receptive. Examples of suitable gene-products include, but are not limited to, herpes simplex virus thymidine kinase, cytosine deaminase, xanthine-guaninephosphoribosyl transferase, purine nucleoside phosphorylase, cytochrome P450 2B1 and their analogs. Other gene products suitable for use in the methods of the present invention will be readily apparent to those of skill in the art.

In a preferred embodiment, the first compound is a prodrug, i.e., a compound to which the cell of interest in not initially sensitive to, but which the gene-product converts into a compound to which the cell of interest is sensitive. Examples of suitable prodrugs include, but are not limited to, ganciclovir, acyclovir, bromovinyldeoxyuridine, 5-fluorocytosine, 6-thioxanthine, MeP-dr and cyclophosphamide. Other prodrugs suitable for use in the methods of the present invention will be readily apparent to those of skill in the art.

In another embodiment, the present invention provides a method of sensitizing a cell to a compound, the method comprising: a) delivering to a cell an enzyme which promotes the processing of a first compound into a second compound; and b) delivering to the cell the first compound in a lipid formulation; wherein the cell is more sensitive to the second compound than the first compound. In a presently preferred embodiment, both the enzyme and the first compound are delivered in lipid formulations.

In yet another embodiment, the present invention provides a composition for treating a human condition (e.g., a human medical disorder or disease state), the composition comprising a prodrug in a lipid formulation and a pharmaceutically acceptable carrier. In a presently preferred embodiment, the composition further comprises a vector or an enzyme in a lipid formulation.

In still another embodiment, the present invention provides a kit for the treatment of a human medical disorder, the kit comprising: a) a vector in a lipid formulation; and b) a prodrug in a lipid formulation.

In addition, the present invention provides methods for preparing lipid formulated prodrugs, vectors and enzymes which can be used in carrying out the methods of the present invention.

Other features, objects and advantages of the invention and its preferred embodiments will become apparent from the detailed description which follows.

BRIEF DESCRIPTION OF THE DRAWINGS

FIG. 11A, liver.

DEFINITIONS

Figure 1:
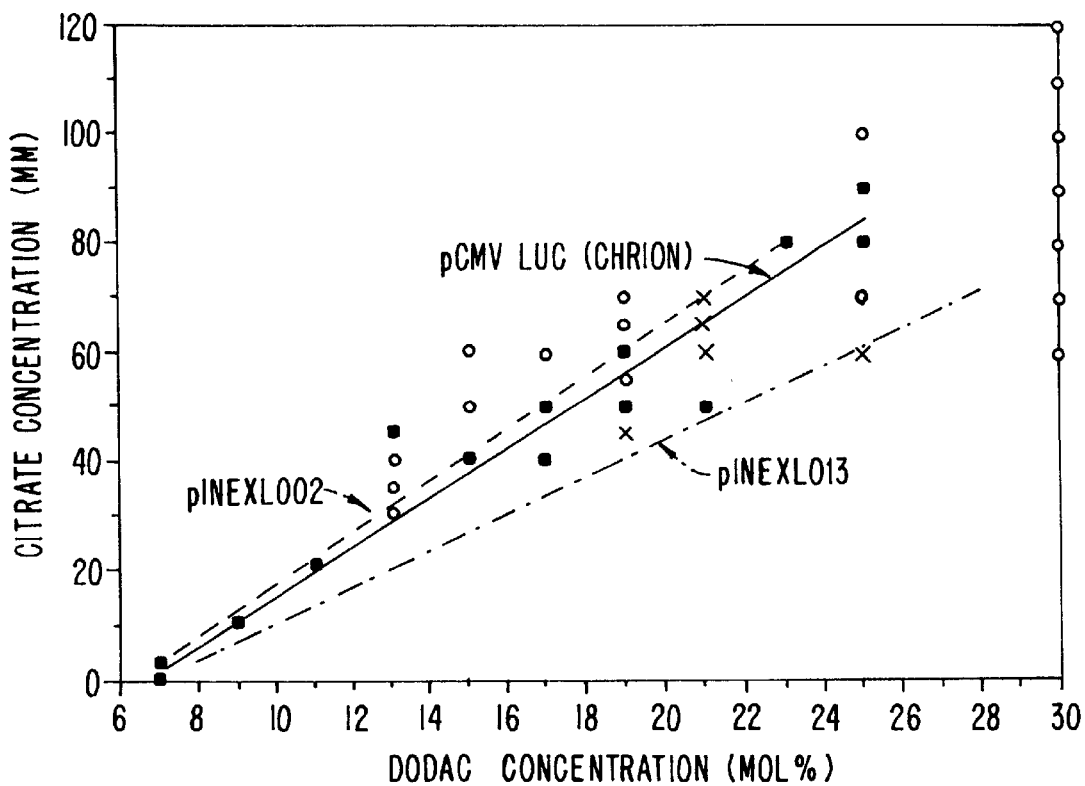
FIG. 1 illustrates the relationship of citrate concentration in the dialysis buffer and the DODAC mol % in the lipid for the preparation of lipid-plasmid particles. The solid dots represent good quality formulations having high association efficiencies (>40%), small size (<100 nm) and low values of size polydispersity (chi-square less than 10, preferably less than 3) on a NICOMP particle sizer. The stars represent formulations containing aggregates or having large polydispersity values, and the open circles represent formulations having low association efficiencies (<40%). Proper tuning of the citrate buffer concentration to the cationic lipid charge appears to improve the formulation. Alternative anionic buffers may also be used if the counterions can prevent the cationic lipid from aggregating during the detergent removal step.

"Sensitizing" refers to the ability to increase the sensitivity of a designated system, such as a cell. This meaning includes changing a cell to make it more responsive to a compound to which it previously was not sensitive or was less sensitive. Sensitizing and "more sensitive" also include increasing the sensitivity of a cell such that exposure to a previously non-killing substance results in cell death.

"Nucleic acid vector" or "vector" refer to a composition comprising a nucleic acid sequence encoding a gene product. This is usually a plasmid or viral genome, but can also include other compositions such as linear nucleic acids, protein/nucleic acid conjugates, etc. Depending on usage, vector can also refer to a nucleic acid delivered in a virus encapsulated or protein coated format, wherein the entire composition is known as a vector.

"Lipid formulation" refers to any lipid composition that can be used to deliver a compound including, but not limited to, liposomes, wherein an aqueous volume is encapsulated by an amphipathic lipid bilayer; lipid particles, wherein the lipids coat an interior comprising a large molecular component, such as a plasmid, with a reduced aqueous interior; or lipid aggregates or micelles, wherein the encapsulated component is contained within a relatively disordered lipid mixture. As used herein, a "lipid encapsulated" can refer to a lipid formulation which provides a compound with full encapsulation, partial encapsulation, or both.

DETAILED DESCRIPTION OF THE INVENTION AND PREFERRED EMBODIMENTS

The present invention provides a qualitative improvement to the GDEPT system by employing lipid formulations for one or both of the vector encoding the gene and the prodrug. In a preferred embodiment of this invention, both the nucleic acid vector and prodrug are delivered separately in lipid formulations. The composition of the lipids in the formulation can be the same or different depending on the desired efficacy. Alternatively, the vector and the prodrug can be delivered together in the same lipid formulation at the same time. The use of a lipid formulation for the prodrug, with or without a lipid formulation for the vector, confers an exquisite sensitivity to GDEPT not previously known.

In general, patient therapy can be achieved using the methods of the present invention as follows. In the first step, a gene product must be expressed in cells at the disease site or target site to increase the sensitivity of such cell(s). The first step therefore requires delivery of the nucleic acid vector to the disease site. Any delivery method known in the art can be employed in the methods of the present invention. Local (regional) delivery can be achieved, for example, by direct injection at the disease site or by inhalation of the vectors, such as naked DNA, modified viruses, cationic lipid-plasmid aggregates, and by other means known to those of skill in the art. For systemic delivery, such as intravenous administration, fully encapsulated lipid-nucleic acid particles are preferred. Such particles offer the advantage of greater biodistribution and prolonged circulation half-lives, and allow delivery of the plasmid to microscopic or otherwise un-injectable disease sites.

Several approaches for introducing nucleic acids into cells in vivo have been used. These include liposome based gene delivery by systemic administration (e.g., parenteral, including intravenous and intraperitoneal delivery), intratracheal instillation, aerosolized gene delivery and the like. For example, Debs and Zhu WO 93/12240, Debs WO 92/1108 and Debs U.S. Pat. No. 5,641,662 all describe aerosolized gene delivery of lipid DNA complexes to mammals. Similarly, Stribling, et al., PNAS 89:11277–11281 (1992), describe lipid delivery to mice. McLachlan, et al., *Gene Therapy* 2:614–622 (1995), describe DOTAP-mediated lipid delivery of hCFTR to mice. Canonico, et al., AM *J. Respir. Cell Mol. Biol.* 10:24–29 (1994), and Canonico, et al., *The American Physiological Society* 415–419 (1994), describe lipofectin-mediated gene delivery of hr1AT to rabbits by aerosolized gene delivery. Alton, et al., *Nature Genetics* 5:135–142 (1993), describe DC-chol:DOPE/ DOTAP-mediated delivery of hCFTR and t-gal by aerosol or tracheal instillation to mice. Capelen, et al., *Nature Medicine*, 1(1):39 (1995), describe delivery of CFTR to the nasal epithelia of humans using a DC-Chol/DOPE mediated procedure, as does McLachlan, et al., *Gene Ther.* 3(12):113–1123 (1996). A variety of reports of administration of lipid-DNA complexes by parenteral administration have also been made, including Brigham WO 91/06309 and U.S. Pat. No. 5,676, 954; and Debs and Zhu WO 93/24640. Accordingly, a variety of procedures for transducing cells in vivo using lipid-mediated techniques are known. Details of preferred formulations are given below.

The local or systemic delivery that is employed to deliver the vector to the cells must ensure that the vector is taken up and expressed sufficiently to sensitize the cell to the prodrug. Those skilled in the art know the variety of vector enhancements that can be used to improve expression of the suicide-gene product. Such enhancements include, but are not limited to, compounds or sequences that assist with intracellular localization of the vector, promoters that improve transcription or translation of the DNA sequence, features that improve the intracellular localization of the gene product, and the like. The full variety of functioning vector possibilities fall within the orbit of this invention.

In the second step, the prodrug in a lipid formulation is delivered to the cells. The use of lipid formulations has many surprising and previously undiscovered advantages over the delivery of free drug in the GDEPT system including, but not limited to, improved targeting to the disease site transfected by the vector, prolonged circulation half-life, increased drug loading, reduced toxicity towards non-target tissues, improved treatment modalities, such as a single bolus injection as opposed to IV drip, and the like. These advantages surmount the clear limitations of the prior art GDEPT systems. Further, the liposomal formulation of the prodrug will preferably provide similar biodistribution to a lipid vector formulation, thereby concentrating both the vector and the prodrug at the disease site.

Usually, the vector will be delivered to the target cell in advance of the prodrug, in order to allow synthesis of the suicide gene product prior to the arrival of the prodrug. Temporal separation can be obtained either by separate administration of vector and prodrug, or by providing the formulations simultaneously, wherein the vector formulation rapidly accumulates at the target site and delivers the vector, and the prodrug formulation accumulates or delivers its payload more slowly. Using the compositions and the methods of the invention, therefore, the vector is delivered to the cell to direct synthesis of the suicide gene product, the cell is thereby sensitized, the prodrug is delivered to the cell, and patient therapy, i.e., reduction of tumor size, inflammation or infectious load and the like, is achieved.

A. Formulating the Nucleic Acid Vector

The nucleic acid vector formulation can be achieved using any prior art method. The preferred methods for systemic (i.e., intravenous or other parenteral) delivery result in a high-efficiency encapsulation, wherein little of the vector is exposed to free solution or adsorbed to the outer surface of the lipid particle. Such methods are disclosed in published PCT Patent Application WO 96/40964, U.S. Pat. No. 5,705,385, and U.S. patent application Ser. Nos. 08/485,458, 08/484,282, 08/660,025, 08/856,374, 60/063,473, 08/996,783, 06/082,665 and 60/086,917, all of which are assigned to the assignee of the instant invention and incorporated herein by reference. Specific embodiments of preferred formulations are set forth in the Examples below. Generally, high efficiency encapsulation provides low immunogenicity and improved tolerance when injected for systemic delivery. Further, these lipid-plasmid particles are relatively easy to characterize and define compared to cationic lipid-plasmid aggregates used in local delivery methods.

B. Formulating the Prodrug

The lipid-prodrug formulation can be achieved by any prior art method. The preferred methods result in a desirable drug:lipid ratio of about 0.1 to 0.25 (mol/mol). The lipid-prodrug formulation can be synthesized using standard freeze-thaw and extrusion techniques disclosed in Hope, et al., *Biochem. Biophys. Acta* 812:55–65 (1985). Other drug loading and encapsulation techniques that can be used are disclosed in U.S. patent application Ser. Nos. 08/399692, 08/607614, 08/588542, 08/741622, the teachings of which are incorporated herein by reference. Sizing of the lipid formulation can be achieved using extruders, pressure cells, and other tools known to those of skill in the art.

Both the vector and prodrug formulations can include components selected from a wide variety of lipids, lipid conjugates and compatible additional components known in the art. Such components can be cloaking agents to reduce elimination by the host immune system, such as ATTA-lipid conjugates disclosed in U.S. patent application Ser. Nos. 08/996,783, filed Dec. 23, 1997 and 06/073,852, filed Feb. 2, 1998, or PEG-lipid conjugates disclosed in U.S. patent application Ser. Nos. 08/486214, 08/316407 and 08/485608, the teachings of which are incorporated herein by reference. These components can also be targeting agents which encourage the lipid formulations to accumulate in the area of the disease or target site. In addition, these components can be compounds which improve features of the formulation, such as leakiness, longevity in circulation, reduction in toxicity, encapsulation efficiency, etc. Examples of these components and others which may usefully be included in the formulations of the invention are known to and used by those skilled in the art.

With respect to both the nucleic acid vectorformulation and the prodrug formulation, it is sometimes preferable to employ a programmable fusogenic lipid formulation. This refers to a formulation which has little tendency to fuse with cell membranes and deliver its payload until a given signal event occurs. This allows the lipid formulation to distribute more evenly after injection into or delivery to an organism or disease site before it starts fusing with cells. The signal event can be, for example, a change in pH, temperature, ionic environment, or simply time. In this last event, the fusion delaying or "cloaking" component, such as the ATTA-lipid conjugate or PEG-lipid conjugate, can simply exchange out of the liposome membrane over time. By the time the formulation is suitably distributed in the body, it is calculated to have lost sufficient cloaking agent so as to be fusogenic. With other signal events, it may be desirable to choose a signal event which is associated with the disease site or target cell, such as increased temperature at a site of inflammation.

The possible lipid components of the prodrug formulations of the invention are all those components typically used in the art including, but not limited to, sphingosomes disclosed in U.S. Pat. No. 5,543,152, and U.S. patent application Ser. Nos. 08/536584, 08/316399, 08/485608, 08/442267.

C. Vector/Prodrug Combinations

Any suicide gene/prodrug combination can be used in the fashion disclosed herein. Several suicide gene/prodrug combinations suitable for use in the methods of the present invention are cited in Sikora in OECD Documents, Gene Delivery Systems at pp.59–71 (1996), incorporated herein by reference, and include, but are not limited to, the following:

| Suicide Gene Product | Less Active ProDrug | Activated Drug |
| --- | --- | --- |
| Herpes simplex virus type 1 thymidine kinase (HSV-TK) | ganciclovir(GCV), acyclovir, bromovinyl-deoxyuridine, or other substrates | phosphorylated dGTP analogs |
| Cytosine Deaminase (CD) | 5-fluorocytosine | 5-fluorouracil |
| Xanthine-guanine-phosphoribosyl transferase (XGPRT) | 6-thioxanthine (6TX) | 6-thioguano-sinemonophosphate |
| Purine nucleoside phosphorylase | MeP-dr | 6-methylpurine |
| Cytochrome P450 2B1 | cyclophosphamide | [cytotoxic metabolites] |
| Linamarase | amygdalin | cyanide |
| Nitroreductase | CB 1954 | nitrobenzamidine |
| Beta-lactamase | PD | PD mustard |
| Beta-glucuronidase | adria-glu | adriamycin |
| Carboxypeptidase | MTX-alanine | MTX |
| Glucose oxidase | glucose | peroxide |
| Penicillin amidase | adria-PA | adriamycin |
| Superoxide dismutase | XRT | DNA damaging agent |
| Ribonuclease | RNA | cleavage products |

Any prodrug can be used if it is metabolized by the heterologous gene product into a compound to which the cell is more sensitive. Preferably, cells are at least 10-fold less sensitive to the prodrug than its metabolite.

A preferred pro-drug is the lipophilic elaidic acid ester analogue of ganciclovir ("E-GCV"). E-GCV has a lipophilic moiety which may enhance encapsulation and delivery of the pro-drug by the pro-drug/liposome formulations of the invention. This enhanced delivery using liposomes may enhance the benefits set out in the research which describes the E-GCV compound and methods for its synthesis: Balzarini, et al., *Gene Therapy*, 5:419–426 (1998).

D. Disease Site Targeting by Systemic Delivery

One of the great advantages of the invention is its versatility in targeting a broad range of disease sites. In particular, lipid encapsulated formulations are usefully employed in targeting and killing tumor cells and other neoplasia, or other cell types that can usefully be sensitized to perform some other function. Other cell types include, but are not limited to, sites of inflammation, sites where genes are aberrantly expressed, sites of infection, etc.

In a preferred embodiment, both the vector and the prodrug are delivered in a lipid encapsulated formulation by intravenous administration. This method takes advantage of the known tendency of lipid encapsulated formulations to accumulate at tumors and neoplasia, even without specific targeting aspects. This ability is thought to be the result of "leaky" vasculature at sites of neoplasia that is easily invaded by small sized lipid particles (see, R. K. Jain, Sci. Am. 271:58–65 (1994)).

Where specific cell type targeting is preferred, the lipid formulation can contain, e.g., on the outer surface, antigens or markers which are recognized by, or which recognize, receptors on the target cell. Examples of such targeting methods can be found in, for example, Forum: Liposome Targeting in Animal Models (Ed. L. Huang), *Journal of Liposome Research* 7(4): 315–534 (1997), the teachings of which are incorporated herein by reference.

Generally, when administered intravenously, the vector and/or the prodrug formulation will be formulated with a suitable pharmaceutical carrier. Many pharmaceutically acceptable carriers can be employed in the compositions and methods of the present invention. Suitable formulations for use in the present invention are found, for example, in *Remington's Pharmaceutical Sciences*, Mack Publishing Company, Philadelphia, Pa., 17th ed. (1985). A variety of aqueous carriers may be used and include, for example, water, buffered water, 0.4% saline, 0.3% glycine, and the like, and may include glycoproteins for enhanced stability, such as albumin, lipoprotein, globulin, etc. Generally, normal buffered saline (135–150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolarnine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration. Carriers may also be employed when delivering the vector or prodrug formulations by other parenteral methods known in the art, such as subcutaneous, intratumoral or intramuscular injection, inhalation, and the like.

The instant invention also demonstrates that encapsulated prodrug will also improve the related system of Antibody Directed Enzyme Prodrug Therapy ("ADEPT") (Bagshawe, K., et al., B. J. Cancer 58:700–703 (1988)). In this system, targeted antibodies are used to deliver enzyme directly to the tumor or disease cell. Often these enzymes function in the extracellular matrix near such cells. At the target site, the prodrug is converted to the toxic metabolite by the enzyme. Clearly, delivery of prodrug in a lipid formulation would have similar advantages to those shown in the GDEPT system, such as syncopation with the gene/enzyme delivery, reduced toxicity, improved targeting, prolonged circulation, and the like.

The invention will be described in greater detail by way of specific examples carried out in accordance with *Canadian Council on Animal Care*, Vol. 2nd Ed., "Guide to the care and use of experimental animals," Eds. Olfert, E., Cross, B. and McWilliam, A. (1993). The following examples are offered for illustrative purposes, and are not intended to limit the invention in any manner. Those of skill in the art will readily recognize a variety of noncritical parameters which can be changed or modified to yield essentially the same results.

EXAMPLES

A. EXAMPLE 1

This examples illustrates the synthesis of lipid-plasmid particles for systemic delivery.

Figure 14A:
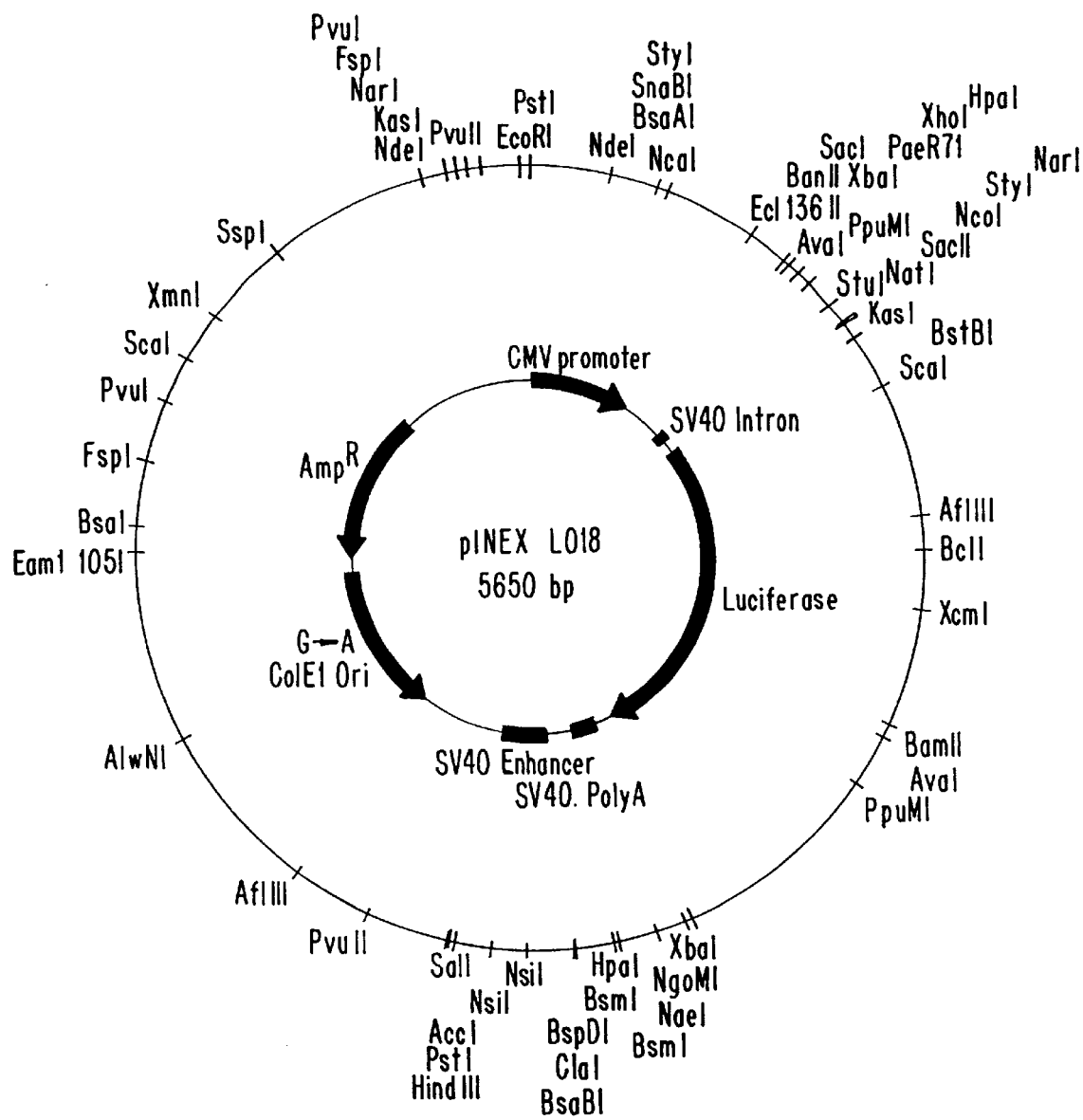
FIG. 14B illustrates pfNEX TK10 plasmid construct.
Figure 14B:
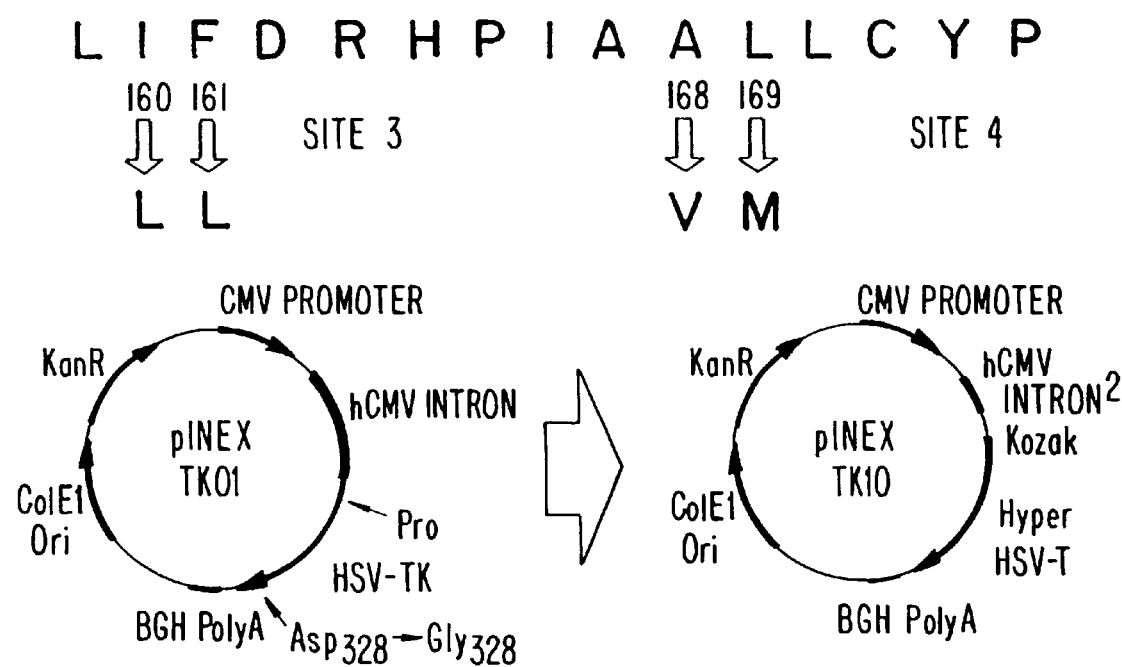

Materials: Plasmids are preferably supercoiled, 4000 to 15000 bp in length, encoding genes and enhancer elements, etc. as desired. The plasmids employed in these examples are:

pINEX L018 - an expression vector in which the *Photinus pyralis* luciferase gene (Promega, Madison, Wis.) is under the control of the CMV promoter. Other genes and sequences are set out in FIG. 14A.

pINEX-TK10 - an expression vector comprising a pBR322 derived plasmid with CMV promoter linked to a "hyper" HSV-TK gene (see, Black, et al., PNAS USA, 93:3525–3529 (1996). Other genes and their orientation are set out in FIG. 14B.

pINEX-IL-12 - is similar to pINEX-TK10 except that the therapeutic gene comprises the IL-12 gene linked to the CMV promoter.

Cationic lipid, N,N-dioleyl-N,N-dimethyl ammonium chloride ("DODAC") and monomethoxy polyethylene2000 glycol succinate-(C8:0-ceramide) ("PEG-Cer-C8") were synthesized at Inex Pharmaceuticals Corp. Dioleyl-phosphatidylethanolamine (DOPE): was supplied by Northern Lipids, Vancouver. Standard dialysis membranes: Spectro/Por 5 regenerated Cellulose (12–14,000 MWCO) was purchased from VWR (Manufactured by Spectrum Medical Industries Inc.). Sodium Citrate was purchased from BDH. Sodium Chloride, Triton X-100 and Octyl-beta-D-glucopyranoside ("OGP") were obtained from VWR Scientific, Fisher Scientific or Sigma Chemical Company. INEX 303 (or, Alternatively, Formulation 1.1)

Plasmid (50–400 µg) is incubated with DODAC in 500 µL of the prep solution containing 0.2 M OGP in 150 mM NaCl; 5 mM HEPES pH 7.4, for 30 min at room temperature. This mixture is added to a mixture of DOPE and PEG-Cer-C14 or PEG-Cer-C20 or PEG-Cer-C8 in 500 µL of the same prep solution. The total lipid concentration was either 5 or 10 mg/ml, with the molar ratio of DOPE:DODAC:PEG-Cer being 84:6:10. The mixture was dialyzed against 150 mM NaCl; 5 mM HEPES (pH 7.4) for 36–48 h with two buffer changes.

Nonencapsulated DNA was removed by anion exchange chromatography on DEAE-Sepharose column (1×4 cm). Empty liposomes were removed by pooling lipid/DNA samples that co-eluted on the DEAE column on top of a sucrose density gradient in 12.5 ml ultracentrifuge tubes. The gradient was formed with 3 ml each of 10% sucrose, 2.5% sucrose and 1% sucrose in HBS layered consecutively from bottom to top. The gradients were centrifuged at 36,000 rpm (160,000×g) for 2 h at 20° C. in a Beckman Optima XL-100K ultracentrifuige using an SW-28 rotor. Separated bands were removed from top to bottom. Fractions were assayed for $^3$H-plasmid and $^{14}$C-CHE by dual-label scintillation counting using a Beckman LS6500 scintillation counter. The lipid encapsulated plasmid DNA banded tightly at the interface between 2.5% and 10% sucrose, while the unassociated lipid was present as a smear from the top of the gradient to the interface between 1% and 2.5% sucrose. The formulation can be concentrated in 12–14,000 MWCO dialysis tubing against 500,000 MW PEG (Aquacide II). When the desired volume is reached, the formulation was transferred into a new dialysis bag and dialyzed overnight against HBS to adjust the NaCl concentration to 150 mM.

INEX 351

Lipid Concentration: 5.0 mg/ml (or 5.3 mM)
Plasmid Concentration: 200 μg
Initial Volume: 1.0 ml
Lipid Stock Solutions: (in 95:5 benzene:methanol, 2:1 chloroform:methanol or ethanol)
By mg, 10–20 mg/ml suitable (10 mg/ml preferred, in the above solvents, absolute ethanol is suitable at these lower concentrations).
Calculated by molarity (dissolved in 95:5 benzene:methanol or 2:1 chloroform:methanol).*
DOPE (744 g/mol): 40 mM
DODAC (582 g/mol): 40 mM
PEG-C8 (2515 g/mol): 20 mM
Formulation for 351: 42.5:42.5:15 (mole %) DOPE:DODAC:PEG-C8

|  | DOPE | DODAC | PEG-C8 |
|---|---|---|---|
| mg | 1.68 | 1.315 | 2.005 |
| mole % | 42.5 | 42.5 | 15 |
| μmol | 2.25 | 2.25 | 0.8 |
| μl | 56.2 | 56.2 | 40 |

Formulation Procedure (1 ml scale):

Aliquot lipid stock solutions into a clean, dry test tube and dry to a lipid film using a stream of $N_2$ gas and then dry under vacuum for at least 2 hrs. Add 50 μL 2M OGP and add 500 μL of 2× strength dialysis buffer, add 200 μg of plasmid and mix by vortexing to dissolve the lipid film. Make up to 1.0 mL with sterile deionized $H_2O$, mix and allow to incubate approximately 30 min at room temperature. Place the solution into a dialysis bag and dialyze for 40–48 hrs against 2 L of dialysis buffer with 1–2 changes of buffer after approximately 24 hrs, and determine the volume of the sample by weighing in a tarred tube (assume density of 1.0). These steps may be followed by DEAE cleaning and/or sucrose density gradient centrifugation, as described above.

After DEAE cleaning and sucrose density centrifugation, as described above, the final INEX 351 formulation has a concentration of about 200 μg/ml plasmid and 5 mg/ml total lipid.

NOTES for INEX 351:

Note 1: Appropriate dialysis buffer concentrations: p53: 150 mM $NaPO_4$+150 mM NaCl(try 140–160 mM NaCl), pH7.4 pLuc: +175 mM NaCl (about 150–170 mM NaCl), pH 7.4

Note 2: 150 mM $NaPO_4$ buffer, pH 7.4: 35.77 g dibasic sodium phosphate ($Na_2HPO_4$) 6.62 g monobasic sodium phosphate ($NaH_2PO_4$) add appropriate quantity of NaCl dissolve in 2 L (final volume) of deionized water with stirring. The final pH may vary between a pH of about 7.3 and about 7.4; this has not normally been adjusted and has not affected the performance of the formulation.

Note 3: Use 0.2 μm filtered buffer with the lipid/plasmid/detergent solution

Note 4: As an alternative to adding 2X dialysis buffer, the plasmid may be pre-dialyzed against dialysis buffer and the formulation may be diluted to its final volume normal strength dialysis buffer. While this means that there will be a slight difference in the buffer concentration, this does not affect the encapsulation efficiency or resulting particle size.

Note 5: If the volume of the formulation is increased (i.e., above 5 mL), add another dialysis change.

Note 6: DEAE-Sepharose columns are often pre-treated by eluting 50 μL of a 10 mg/ml extruded or sonicated 1:1 phosphatidylcholine:cholesterol vesicle formulation (diluted in 2 mL) to block any nonspecific lipid binding to the column.

To reduce the cationic surface charge of INEX 351 formulations, it may be desirable to reduce the amount of cationic lipid (i.e., DODAC) employed. If the amount of DODAC is changed, the amount of DOPE is changed to maintain the same total amount of lipid. Formulations below 30% DODAC are preferably made in 10 mg total lipid. Dialysis buffer may be changed as in Table 1, below:

TABLE 1

Characterization of representative large scale formulations.

| Conc. | Starting volume | Buffer | Encapsulation efficiency | Nicomp particle size (nm)[a] |
|---|---|---|---|---|
| 42.5% | 30 ml | 150 mM $NaPO_4$, 130 mM NaCl | 49% | 131 |
| 30% | 12 ml | 150 mM $NaPO_4$ | 56.8% | 109 |
| 24% | 30 ml | 130 mM $NaPO_4$ | 50.7% | 250 |
| 20% | 15 ml | 105 mM $NaPO_4$ | 63% | 178 |

[a]Nicomp analysis of mean particle size, gaussian dist., volume weighting, before DEAE cleaning and isolation.

INEX 321

Lipid-plasmid particles with 10–30% DODAC are also useful in the present invention. These may be formulated, as described above, or as follows.

Lipid stock solutions: Individual stock solutions of each lipid were dissolved in chloroform/methanol (2:1 v/v) to a final concentration of 2 or 20 mg/ml.

OGP solution: 1.0 M OGP solution was prepared in MilliQ grade water.

Citrate buffer: Sodium citrate buffer was used for dialysis to remove detergent from the formulation. The citrate concentrations were varied according to the amount of DODAC. Buffer also contains 150 mM NaCl and 5 mM HEPES at pH 7.4, unless indicated otherwise. In general, a 10× solution was prepared and diluted 1:10 in MilliQ Plus water for dialysis using a graduated cylinder.

Preparation of lipid/DNA/OGP mixture: A typical formulation contained 10 mg of lipid of DODAC/DOPE/PEG-Cer-C8 and 200 μg DNA. Appropriate amounts of stock solutions containing DODAC, DOPE and PEG-Cer-C8 (normally 15 mol % in this formulation) were mixed in a glass test tube. If the amount of DODAC is changed, the amount of DOPE is changed to maintain a total of 10 mg lipid. The solvent was first removed under a stream of $N_2$ gas followed by incubation under vacuum for 3–5 h. To the lipid, 0.2 mL of 1 M OGP was added. The suspension was vortexed until the lipid was totally dissolved and the solution became clear. Then a 0.2 mL DNA (1 mg/ml) solution containing 200 μg DNA and 0.6 mL HBS (HEPES buffered saline) or citrate buffer (concentrations designated in FIG. 1) were added to a final total volume of 1 mL. If the solution did not become clear, a small amount of OGP (50 μL) was added. The solution was incubated at room temperature for 1 hr to allow the components to equilibrate.

Dialysis: Dialysis tubes were soaked in 60% ethanol (or in distilled water if sterilization was not required) for 30 min. The mixture of DNA/lipid/OGP solution was then transferred to the dialysis tube. The sample was dialyzed for 2 days in 2–4 L citrate buffer (concentration as described in FIG. 1) with two changes of buffer daily.

After preparation, empty liposomes can be removed by DEAE cleaning and sucrose density centrifugation, as described above. Having been taught the various lipid-plasmid particle formulations suitable for systemic delivery in this example, it would be obvious to one skilled in the art to modify them, for example, for improved plasmid delivery and/or intracellular expression using one or more possible variations. Variations of the following type are suggested: percentage of PEG-lipid; size of PEG; length of hydrophobic (anchor) chain; pH sensitive PEG-lipids; replacement of PEG by ATTA (disclosed in U.S. patent application Ser. Nos. 08/996,783, filed Dec. 23, 1997, and 06/073,852, filed Feb. 2, 1998, all of which are assigned to the assignee of the instant invention; addition of membrane modifying lipids, such as cholesterol or DOPE; use of alternative cationic lipids, such as DMRIE, DOTAP, DOTMA, DODMA, AL-1, etc.; use of fusogenic components, such as pH sensitive lipids, peptides (EALA) or polymers (PEAA); use of targeting agents; use of DNA condensing peptides (i.e., polylysine or spermine) or polymers (i.e., PEI); use of negatively charged lipids, such as phosphatidylserine; or use of alternative PEG-lipid linkers, such as SPDP or PDPH (disclosed in U.S. patent application Ser. No. 08/536,584, which is assigned to assignee of the instant invention).

B. EXAMPLE 2

This example illustrates the measurement of the therapeutic effect of lipid formulated ganciclovir on subcutaneous tumors transfected with lipid encapsulated HSV-TK.

| Group | Tumor | Plasmid | Prodrug | Route | Assay | Mice per Group |
|---|---|---|---|---|---|---|
| A | B16 | L018 | PBS | IV | Tumor Volume | 6 C57 |
| B | B16 | L018 | GCV | IV | Tumor Volume | 6 C57 |
| C | B16 | pTK010 | PBS | IV | Tumor Volume | 6 C57 |
| D | B16 | pTK010 | GCV | IV | Tumor Volume | 6 C57 |

On day zero, 24 female C57 mice (Harlan Sprague Dawley, Inc., Indianapolis, Ind.) are seeded sub-cutaneously with 100,000 B 16 mice melanoma cells (NCI catalog B16BL-6) in a total volume of 50 μL (groups A, B, C, D). Tumor volume is determined daily by measuring the length, width and height of the tumor with skin calipers as soon as possible and every day thereafter. Groups A to D are treated with 200 μg plasmid of the appropriate lipid-formulated plasmid, formulated according to Example 1, once daily beginning at 9:00 a.m. on day five and on every day following. The plasmid formulation is injected IV in the tail vein in a total volume of 200 μL PBS. Groups B and D are treated with lipid formulated ganciclovir, prepared according to Example 3, once daily beginning at 3:00 p.m. on day five and on every day following. 0.5 mg ganciclovir (~25 mg/kg) are injected IV in the tail vein in a total volume of 200 μL PBS. On day 21, mice are sacrificed. Tumors are collected and weighed.

The results obtained demonstrate that the mice of group D either did not develop tumors, or else developed tumors significantly more slowly than mice of control group C.

C. EXAMPLE 2A

This example illustrates the measurement of therapeutic effect of systemic delivery of lipid formulated ganciclovir on SCID mice having human (SKOV-3) intraperitoneal (IP) tumors.

| Group | Tumor | Plasmid | Prodrug | Route | Assay | Mice per Group |
|---|---|---|---|---|---|---|
| A | SKOV-3 | L018 | PBS | IV | Tumor Volume | 6 C57 |
| B | SKOV-3 | L018 | GCV | IV | Tumor Volume | 6 C57 |
| C | SKOV-3 | pTK010 | PBS | IV | Tumor Volume | 6 C57 |
| D | SKOV-3 | pTK010 | GCV | IV | Tumor Volume | 6 C57 |

On day zero, 24 female C57 mice are seeded intraperitoneally with 5,000,000 SK-OV-3 human ovary adenocarcinoma cells (ATCC HTB-77)) in a total volume of 500 μL (groups A, B, C, D). Groups A to D are treated with 200 μg plasmid of the appropriate lipid-formulated plasmid, formulated according to Example 1, once daily beginning at 9:00 AM on day five and on every day following. The plasmid formulation is injected IV in the tail vein in a total volume of 200 μL PBS. Treatment will continue for two weeks.

Groups B and D are treated with lipid formulated ganciclovir, prepared according to Example 3, once daily beginning at 3:00 p.m. on day five and on every day following. 0.5 mg ganciclovir (~25 mg/kg) are injected IV in the tailvein in a total volume of 200 μL PBS.

Mice are monitored for survival. If tumors develop, mice are sacrificed and the tumors are collected and weighed.

The results obtained demonstrate that the mice of group D either did not develop tumors, or else developed tumors significantly more slowly than mice of control group C.

D. EXAMPLE 3

This example illustrates the protocol for the preparation of lipid formulated ganciclovir in a sphingomyelin/cholesterol lipid formulation.

1. Weigh out lipids slightly in excess of what is needed. For a 1 mL preparation, use 100 mg (180 μmole) of lipid. 55 mol % is sphingomyelin (99 μmoles, ) and 45 mol % (81 μmoles) is cholesterol (Northern Lipids, Vancouver, BC). Dissolve each lipid in 1 mL of chloroform. Aliquot the required amounts of each lipid into one tube to obtain a 55/45 SM/Chol mixture.
2. Add 4500 dpm/μmole of lipid of $^{14}$C-CHE ($^{14}$C-cholesteryl hexadecyl ether).
3. Dry the lipid to near dryness under nitrogen.
4. Apply to the lyophilizer overnight.
5. Make up a 30/70% solution of ethanol/HBS (HBS is 20 mM Hepes, 145 mM NaCl, pH 7.45)
6. Dissolve 100 mg ganciclovir (109 mg ganciclovir-Na, Hoffmnan LaRoche Ltd.) in 1 mL of 30/70% ethanol/HBS. Vortex well. Add 42000 dpm/μmole $^{3}$H-GCV (7.5 μL of a 1 μCi/mL stock)
7. Add ganciclovir solution to the lipid film and vortex well. Vortex until the solution appears homogeneous.
8. Freeze-thaw for 5 cycles (liquid nitrogen and 65° C.). Warm the cryovial up slightly before putting in the water bath.
9. Take 2–10 μL pre-extrusion samples and assay for radioactivity using the dual label program. Take note of the final volume and use this to determine specific activity for both the lipid and GCV.

10. Extrude the sample 2×thru 3×100 nm filters at 65° C. at 350psi. At this point the sample becomes quite viscous. Add 1 mL HBS to the samples and mix by pipetting up and down.
11. Continue extrusion for a total of 10 passes.
12. Take 2≧10 μL post-extrusion samples and assay for radioactivity.
13. Hydrate some dialysis tubing (MW cutoff 12,000–14,000) in dH$_2$O for 15 min.
14. Put the extruded sample in the tubing and dialyze for 1 hr against 2 L HBS
15. Change to fresh buffer and dialyze overnight.
16. Take 2–10 μL samples and assay for radioactivity
17. Determine the percentage loading by comparing the pre-extrusion and post-dialysis ratios of $^3$H/$^{14}$C. For example: $^3$H/$^{14}$C pre-extrusion=12.0; $^3$H/$^{14}$C post-dialysis=1.2; 1.2/12.0×100%=10% encapsulation.

E. EXAMPLE 3A

Stable transfection of B 16 tumor cells with HSV-TK, for use in Examples 4 and 4A, is achieved as described in Short Protocols in Molecular Biology, Third Edition, page 9–13 to 9–15, or as described therein, with the following modifications. According to the method, the following materials were used:

Plasmids: pCMVTKIRESneo includes a CMV promoter, HSV-TK gene, internal ribosome entry site and neomycin resistance gene. L018 is the same, but with a luciferase gene in place of HSV-TK.

1. Plate B 16 murine melanoma cells in a tissue culture flask (T-75) at 5×10$^5$ cells/flask in 10 ml MEM media with addition of 10% FBS and Glutamine and grow overnight in CO$_2$ incubator at 37° C. to 70% confluency.
2. Aspirate media and feed cells with 3.8 ml fresh media per flask 2 hrs prior to transfection.
3. Prepare plasmid/lipid Lipofectin (GIBCO BRL) aggregate in polystyrene tube according to manufacturer's instructions as follows:
    dilute plasmid to 20 μg/ml in sterile distilled water.
    use Luciferase L018 plasmid as a control for selection in Geneticin (G418), use Thymidine Kinase (neomycin) 20A for TKneo stable cells.
    dilute lipid to 1 mM in sterile distilled water.
    dilute lipid to charge ratio 1 in sterile distilled water (1.2 ml lipid/8 ml water).
    add volume of DNA (20 mg/ml) to equivalent volume of lipid (CR1) dropwise while vortexing.
    incubate DNA/lipid complex for 30 min at room temperature.
4. Slowly add 1.2 ml DNA/lipid complex/T 75 flask, mix gently and incubate 24 hr in CO$_2$ incubator at 37° C. (complex is diluted 1:4 in media).
5. Aspirate media, wash with PBS buffer and split each T75 flask into 2–100×20 mm tissue culture dishes
6. 24 hr after plating into dishes, add the selective agent, Geneticin(G418), at the appropriate concentration to kill nontransfected cells, yet allow cells with transfected TKneo to stay alive. The Luciferase control cells should die.
7. Every 2–3 days, change the media to remove dead cell debris.
8. Within 10 days, clones are visible on bottom of 100 mm dish which are neomycin resistant and TK positive.
9. Scrape clones into 1 ml media in 24-well plate and expand up into T-75 flask.
10. Cells that stably express TK may then be used for local, regional or systemic injection into mice.
11. To screen identified clones for TK expression:
    plate 2000 cells/well in 96 well plate in 150 μL volume and grow 48 hr in CO$_2$ incubator at 37° C.
    add the specific prodrug for TK, ganciclovir, in a dilution series across the plate made up at 2.5× concentrated and add 100 μL/well (add to 150 μL volume)
    incubate 3 days in CO$_2$ incubator at 37° C.
    aspirate media from wells and add Alamar Blue as per manufacturers instructions (Biosource International) (1:10 dilution in media).
    100 μl/well and incubate for 1,2,4 hr and read plate at time intervals on fluorescent plate reader (550,595 nm; 750V; 70 offset; 100 ms integration time).

F. EXAMPLE 4

This example illustrates the effects of systemically delivered lipid-formulated ganciclovir on tumor growth in mice having B16 intradermal tumors stably transfected with HSV-TK.

| Group | Tumor | Prodrug | Route | Assay | Timepoint (assay) | Mice per Group |
| --- | --- | --- | --- | --- | --- | --- |
| A | B16 | PBS | IV | Tumor Volume | DAILY | 8 C57 |
| B | B16 TK | PBS | IV | Tumor Volume | DAILY | 8 C57 |
| C | B16 | LIPO-GCV | IV | Tumor Volume | DAILY | 8 C57 |
| D | B16 TK | LIPO-GCV | IV | Tumor Volume | DAILY | 8 C57 |

32 female C57 mice (Harlan Sprague Dawley, Inc., Indianapolis) were seeded intradermally with B16 tumor cells stably transfected and expressing HSV-TK (prepared as in previous example) at a dose of 150,000 cells in a total volume of 50 μL phosphate buffered saline on day zero. Intradermal tumor volume was determined daily by measuring the length, width and height of the tumor with skin calipers as soon as possible and every day thereafter.

The mice were treated with the ganciclovir prodrug, lipid formulated as in Example 3, once every two days beginning on day four and on every second day following. The ganciclovir dosage of 0.5 mg (~25 mg/kg) was injected IV in a total volume of 200 μL PBS (phosphate buffered saline). Mice received a total of nine treatments. On day 21, mice were sacrificed. Tumors were collected and weighed prior to fixation for sectioning.

Intradermal tumors stably transfected with HSV-TK showed no measurable growth when treated systemically with lipid formulated ganciclovir. Untreated B16 tumors, and treated B16 tumors without TK, were not effected by the drug.

G. EXAMPLE 4A

This study was to determine the effect of lipid formulated ganciclovir on TK gene expression in B16 tumor cells stably transfected with HSV-TK and implanted intravenously.

| Group | Tumor | Prodrug | Route | Assay | Timepoint (assay) | Mice per Group |
|---|---|---|---|---|---|---|
| A | B16 TK | PBS | IV | Tumor Volume | DAILY | 8 C57 |
| B | B16 TK | LIPO-GCV | IV | Tumor Volume | DAILY | 8 C57 |

16 female C57 mice were seeded with B16 tumor cells stably expressing HSV-TK by tail vein injection at a dose of 150,000 cells in a total volume of 200 μL phosphate buffered saline on day zero. The mice were treated with the ganciclovir prodrug, lipid formulated as in Example 3, once every day beginning on day two and on the two days following. The ganciclovir dosage of 0.5 mg (~25 mg/kg) was injected IV in a total volume of 200 μL PBS (phosphate buffered saline). Mice received a total of three treatments. On day 21, mice were sacrificed and tumors were scored. Livers, lungs, spleen and pancreas were photographed.

The metastatic tumor nodules of the mouse treated with the lipid-ganciclovir formulation were significantly smaller than those of the untreated mice.

H. EXAMPLE 5

This example illustrates gene expression in distal metastatic tumors using INEX 303 lipid plasmid particles.

Figure 2:
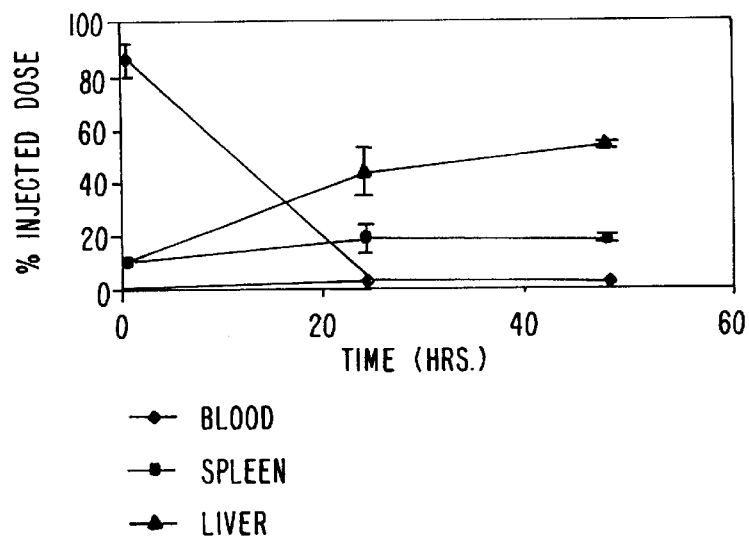
FIG. 2 illustrates the biodistribution in various organs (i.e., blood, spleen and liver) of 303i in C57-Lewis Lung mice.
Figure 3:
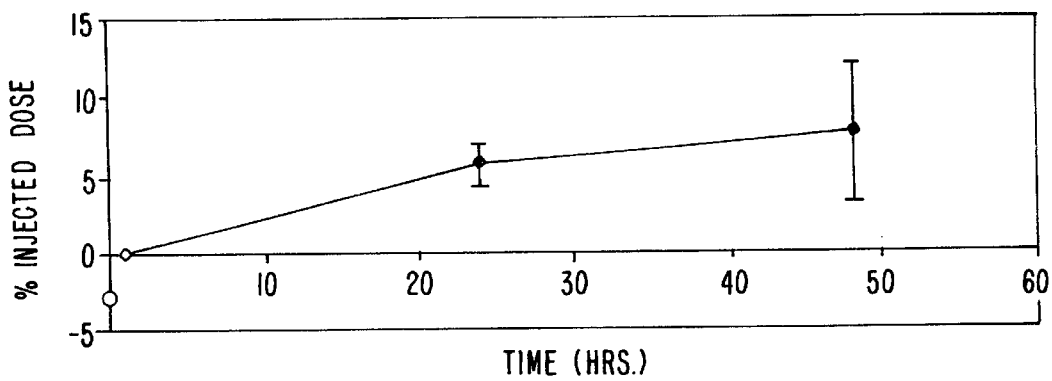
FIG. 3 illustrates the accumulation of 303i at the tumor site in C57 mice.
Figure 4:
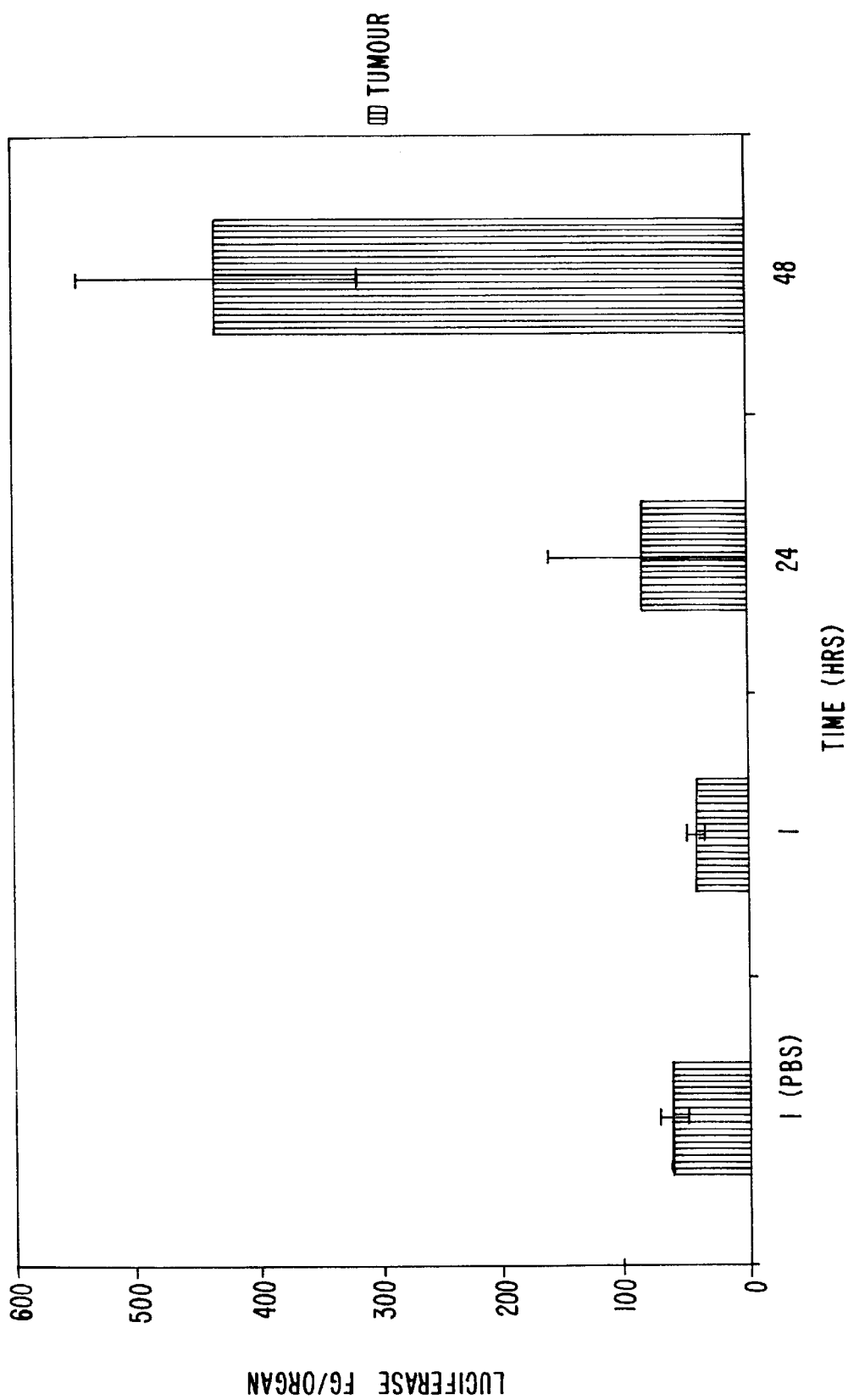
FIG. 4 illustrates a time course of gene product activity at distal (metastatic) tumor sites.
Figure 5:
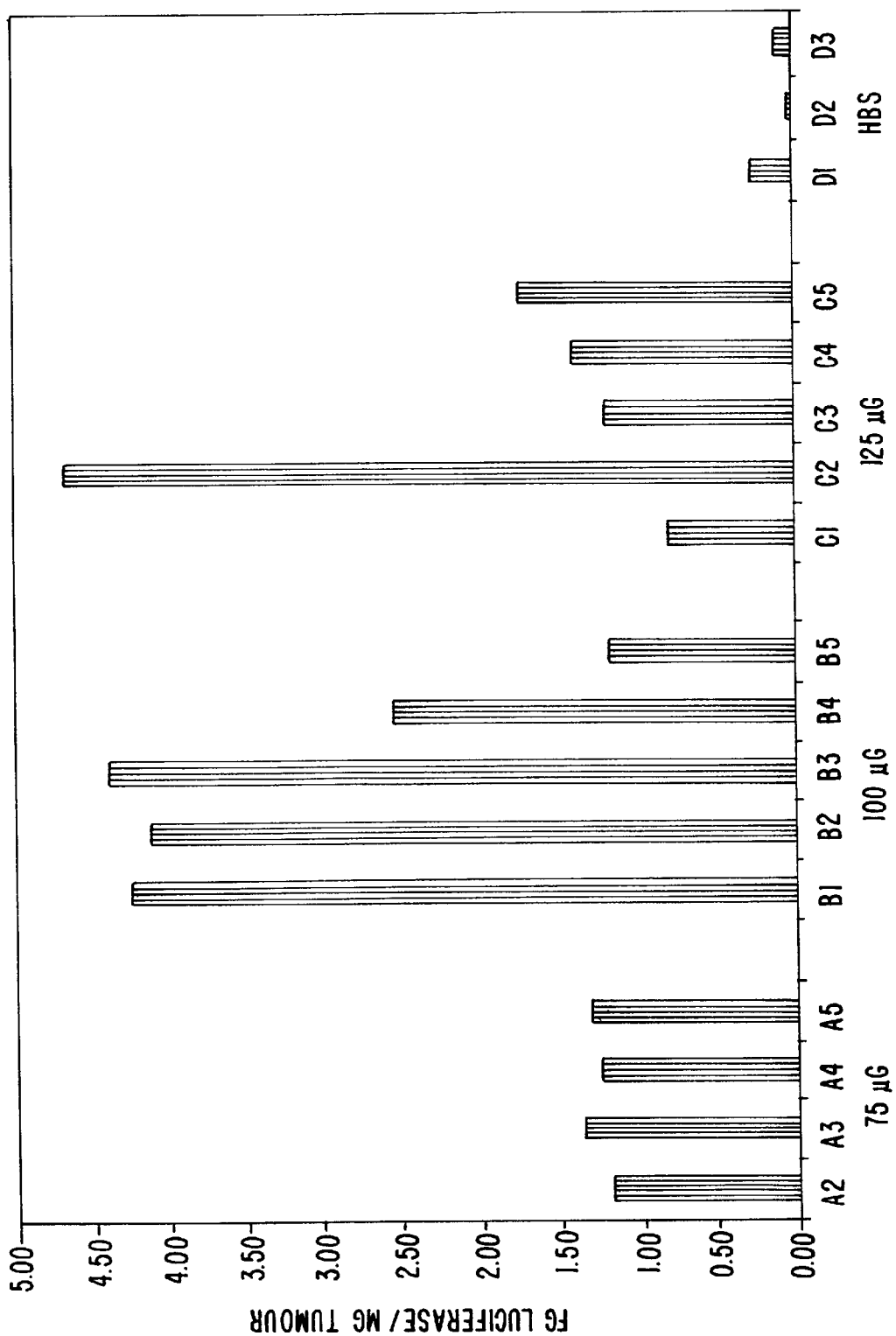
FIG. 5 illustrates gene expression in LS 180 tumors (dose response of 303i after 48 hrs).

On day zero, C57BL/6 mice (Harlan Sprague Dawley, Inc., Indianapolis, Ind.) are seeded with 300,000 LL/2 (Mouse Lewis Lung Carcinoma) cells (ATCC CRL-1642) by intravenous/tail vein injection with total volume 200 μL. On day 10, the mouse is intravenously injected with INEX 303 μplasmid-lipid particles, formulated according to Example 1. The particles carry plasmid L018, which is a standard construct containing the luciferase gene linked to the CMV promoter. At various time points after plasmid injection, mice are sacrificed, and organs and tumors are quickly frozen in liquid nitrogen, then stored at −70° C. Organs/tumors are assayed for the luciferase gene to demonstrate delivery to the organ/tumor site. Biodistribution results for organs are shown in FIG. 2. Accumulation at the tumor site is illustrated in FIG. 3. Southern blot data shows presence of intact plasmid at the tumor site increasing to at least 96 h. Cell protein from organs/tumors is also prepared and assayed for luciferase according to standard techniques. A time course of gene product activity at distal (metastatic) tumor sites is demonstrated in FIG. 3.

I. EXAMPLE 6

This example illustrates the systemic vector delivery and gene expression in an in vivo human tumor.

SCID mice (Harlan Sprague Dawley, Inc., Indianapolis, Ind.) are seeded with 1×10⁶ LS180 human colon adenocarcinoma cells (ATCC CL-187) by subcutaneous injection on day zero. On day 11, mice in groups A, B and C are injected intravenously with indicated doses of L018 μplasmid in lipid formulation INEX 303, which is formulated according to Example 1, in 200 μL total volume. On day 17, mice in group D and E are injected intravenously with L018 plasmid in lipid formulation INEX 320, using C8 or C20 PEG-Cer according to Example 1, in 200 μL total volume. At the times indicated after plasmid injection, mice are sacrificed and organs (liver, spleen and lungs) and tumors are harvested. Expression of the enzyme luciferase is assayed according to standard techniques on all samples.

| Group | Formulation | Assay | Time Point | Mice per group |
|---|---|---|---|---|
| A | 303 (75 μg) | Luciferase | 48 hr | 5 |
| B | 303 (100 μg) | Luciferase | 48 hr | 5 |
| C | 303 (125 μg) | Luciferase | 48 hr | 5 |
| D | 320 (100 μg) | Luciferase | 24 hr | 4 |
| E | 320 (100 μg) | Luciferase | 48 hr | 4 |
| F | PBS | Luciferase | 48 hr | 1 |

J. EXAMPLE 7

This example demonstrates systemic delivery and expression at an in vivo tumor site of a vector containing the HSV-TK gene, using a lipid-nucleic acid particle prepared according to Example 1.

C57 mice are intraperitoneally seeded with 100,000 B16 tumor cells in a total volume of 200 μL PBS on day zero. On day 14, test mice are injected with INEX 351 μplasmid formulation (100 μg DNA in 500 μL PBS) prepared according to Example 1. The plasmid vector used is pCMVT-KIRESneo as described earlier. 24 h later, mice are sacrificed, and tumors are isolated, fixed within 5 minutes, and prepared in paraffin sections using standard techniques. The expression of the HSV-TK gene at the distal tumor site is assayed by in situ RNA/RNA hybridization using techniques standard in the art. One such technique is summarized below.

Figure 6A:
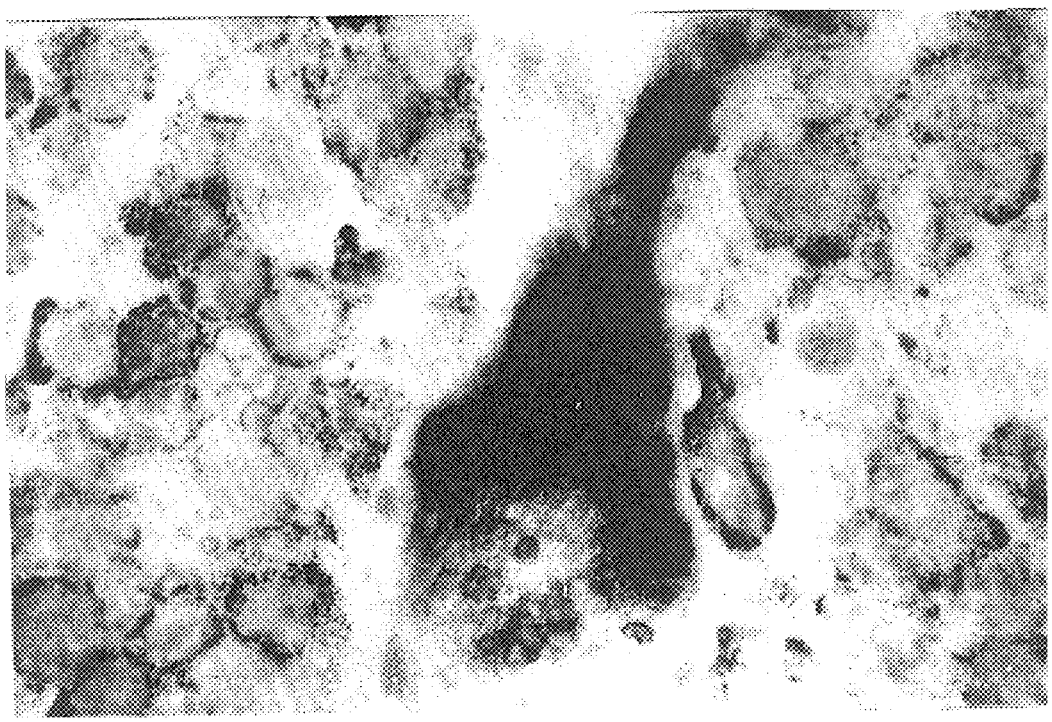
FIG. 6 illustrates the pattern of HSV-TK gene expression within peritoneal tumors.
Figure 6B:
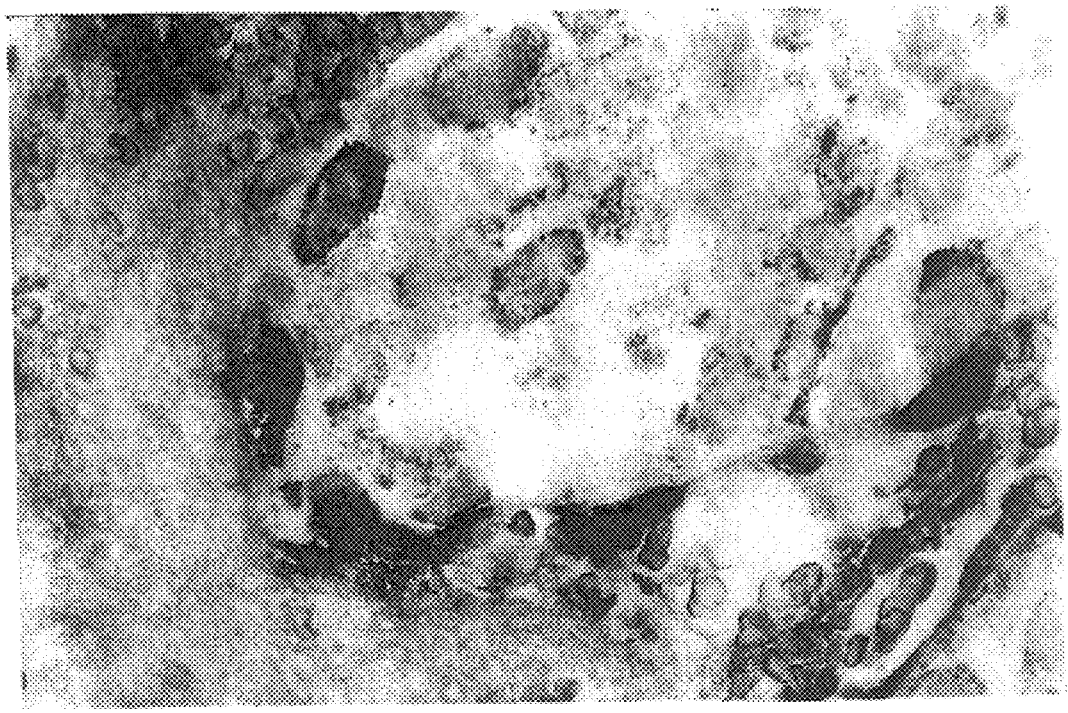

The pattern of HSV-TK gene expression within peritoneal tumors is demonstrated in FIG. 6. In all cases of gene expression, positive signal is observed as a cellular content of B16 cells or endothelial cells. Positive stained cells are localized in proliferative zone associated with blood vessels or peripheral area.

Protocol for RNA/RNA in Situ Hybridization of in Vivo Tumors Transfected by Systemically Delivered Plasmid.

Tumors are prepared for in situ investigation by paraffin embedding and staining. Specifically, peritoneal tumors are collected into 4% paraformaldehyde/PBS fixative (Sigma Chemical Co.) and fixed overnight at 4° C. Serial 5 μm sections are prepared after the samples have been dehydrated in graded ethanol solutions, cleared in chloroform and embedded in paraffin wax (Paraplast Plus, Fisher).

When ready to be used, prepared samples are treated with two changes of xylene for 10 min., each followed by rehydration in graded ethanol solutions to 50% ethanol. Samples are prehybridized by standard rinsing, incubation with 0.1 M triethanolamine (TEA) buffer, pH 8.0, containing 0.25% (v/v) acetic anhydride, followed by treatment at 56° C. for at least 60 minutes in hybridization buffer containing: 40% deionized formamide, 10% dextran sulfate, 1×Denhardt's solution (0.02% Ficoll, 0.02% polyvinylpyrrolidone, 10 mg/ml RNase- free bovine serum albumin), 4×SSC, 10 mM DTT, 1 mg/ml yeast t-RNA, and 1 mg/ml denatured and sheared salmon sperm DNA.

Labelling of RNA probe by in vitro transcription of DNA was done as follows. The fragment of 599bp (532–1131) from HSV-TK (pTK10) was cloned into KpnI and BamHI sites of the vector pGEM-7Zf(+) (pTK11). The plasmid is cloned by standard techniques and prepared using Qiagene 500 (Qiagen, Inc.). For the anti-sense probe, this plasmid is linearized by cutting it with KpnI at the original 5' end of the cDNA HSV-TK and purified. The same logic is used for sense (control) probe (i.e., cut at the side of the 3-end of insert by BssHII or BamH or SacI). The plasmid is purified by ethanol precipitation. The following are then mixed in a 1.5 mL sterile RNase free microcentrifuge tube on ice: 4 µL (4 µg) purified, linearized plasmid DNA, 5 µL of 10×concentrated DIG RNA Labeling Mix (supplied by manufacturer), 10 µL 5×concentrated Transcription Buffer (400 mM Tris-HCl (pH 8.0, 20° C.), 60 mM MgCl$_2$, 100 mM Dithiothreitol (DTT), 20 mM spermidine, 2 µL RNasin, 3 µL RNA polymerase (SP6 for antisense or T7 for sense), and sterile, redistilled water to make a total reaction volume of 50 µL.

The components are mixed and centrifuged briefly, and then incubated for 2 hrs at 37° C. (for T7 RNA polymerase) or at 40° C. (for SP6 polymerase). Note: Longer incubations do not increase the yield of labeled RNA. To produce larger amounts of RNA, scale up the reaction components. After incubation, add 3 µL DNase I, RNase free and 1 µL RNasin to the tube and incubate for 15 min at 37° C. Then add 2.5 µL 0.5M EDTA (pH 8.0) to the tube to stop the polymerization reaction.

The labeled RNA transcript is precipitated by performing the following steps. Add to the reaction tube 6.25 µL 4 M LiCl and 180 µL prechilled (−20° C.) 100% ethanol incubate overnight at −70° C. Centrifuge the tube (at 13,000×g) for 15 min at 4° C. Discard the supernatant. Wash the pellet with 50 µL ice-cold 70% (v/v) ethanol. Centrifuge the tube (at 13,000×g) for 5 min at 4° C. Discard the supernatant and dry the pellet at room temperature. Dissolve the RNA pellet for 30 min at 37° C. or (R.T.) in 20 µL DEPC (diethylpyrocarbonate)-treated, sterile, redistilled water, and add 20 µL deionized formamide and 1 µL RNasin. Keep transcript at −20° C. or −70° C.

An accurate quantification of DIG-labeled RNA obtained in the labeling reaction is most important for optimal and reproducible results in various membrane or in situ hybridization techniques. Too high of a probe concentration in the hybridization mix usually causes background, while too low of a concentration leads to weak signals. The estimation of yield can be performed in a side by side comparison of the DIG-labeled sample nucleic acid with a DIG-labeled control that is provided in the labeling kits. Dilution series of both are prepared and spotted on a piece of membrane. Subsequently, the membrane is calorimetrically detected. Direct comparison of the intensities of sample and control allows the estimation of labeling yield.

The hybridization reaction is then performed. Drain pre-hybridization buffer from the pre-hybridized slides and overlay each section with 200 µL of hybridization buffer containing 0.2–1 ng of digoxigenin-labeled RNA probe (0.2 ng/µL). Cover samples with a 24×30 mm hydrophobic plastic coverslip. Incubate sections at 56° C. overnight in a humid chamber. Washes may include an RNAse step which reduces the background, but decreases the signal as well. It is important to keep the tissue sections moist at all times during washing.

Wash the slides in 2×SSC at 55° C. for 30 min.
Wash in 50% formamide, 2×SSC at 65° C. for 30 min.
Wash in 2×SSC 3 times at 37° C. for 5 min. each.
Wash in RNase 10 µg/ml washing solution at 37° C. for 30 min.
Wash in 50% formamide, 2×SSC at 65° C. for 30 min.
Wash in 2×SSC at 37° C. for 15 min.
Wash in 0.2×SSC 5 times at 37° C. for 5 min. each.

After hybridization, cells are incubated DIG-specific antibody. Wash the slides in TBS at RT for 30 min. Incubate sections with blocking solution (TBS and 2% goat serum) at RT for 1 h. Decant blocking solution and incubate sections with goat anti-DIG-alkaline phosphatase (Fab fragment) dilution 1:500 at RT for 1 h. Wash the slides in TBS at RT for 30 min.

Wash the slides in substrate buffer (100 mM Tris-HCl (pH 9.5), 100 mM NaCl, 50 mM MgCl$_2$) at RT for 30 min.

Prepare a color solution containing: 10 ml substrate buffer,50 µL NBT (nitroblue tetrazolium) and 37 µL BCIP. Slides are immersed in color solution at room temperature for 1–2 hr or at 4° C. for 2–3 days. Slides are washed with water and observed by light microscopy. Results are shown in FIG. 6.

K. EXAMPLE 8

Figure 7A:
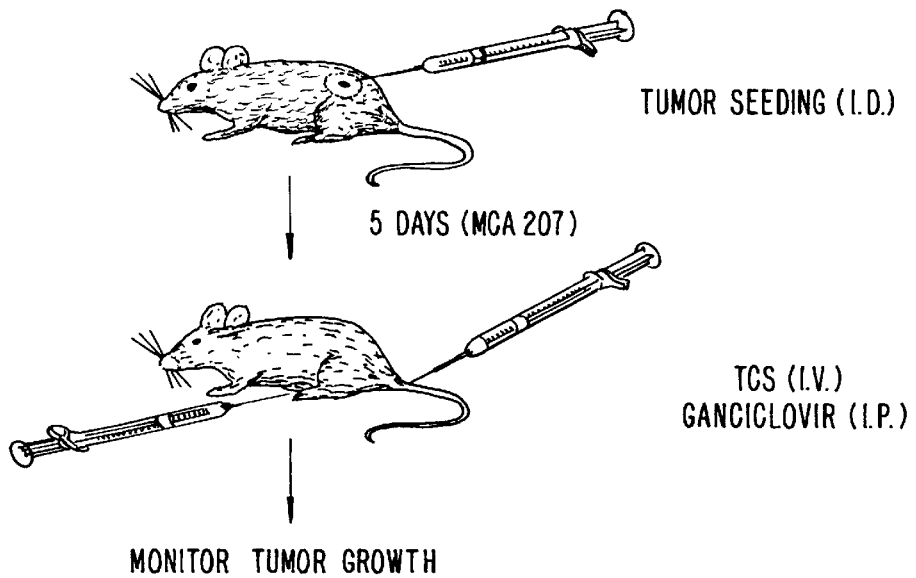
FIG. 7(A) illustrates in vivo efficacy studies using a tumor model.
Figure 7B:
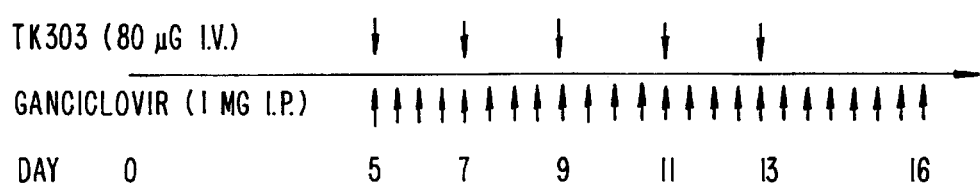
FIG. 7(B) illustrates a 1 6-day treatment regimen on test mice after tumor inoculation.

This example describes the treatment of tumors using the method of the present invention. In particular, this example demonstrates the effect of pINEX-TK10 in Formulation 1.1 in inhibiting the growth of MCA-207 tumors following treatment with ganciclovir. The general method is set out in FIGS. 7A and 7B.

The pINEX-TK10 construct consists of a pBR322 derived plasmid containing a CMV promoter linked to a "hyper" HSV-TK gene, bovine growth hormone polyadenylation sequence and kanamycin resistance gene. "hyper" HSV-TK is a more active form of the HSV-TK gene as disclosed by Black, et al., PNAS (USA), 93:3525–3529 (1996). The plasmid construct employed is set forth in FIG. 14B.

| Group | Formulation | GCV | Route* | Assay | Time-point | # of Mice |
|---|---|---|---|---|---|---|
| A | PBS | PBS | IP | Volume/CTL | — | 6 C57 |
| B | Empty 1.1 | PBS | IP | Volume/CTL | — | 6 C57 |
| C | 1.1 TK | PBS | IP | Volume/CTL | — | 6 C57 |
| D | 1.1 TK | GCV | IP | Volume/CTL | — | 6 C57 |

*It is noted that the "Route" refers to the delivery of the prodrug, i.e., gangciclovir.

24 female C57 mice were seeded with 100,000 MCA-207 fibrosarcoma tumor cells (provided by S. Rosenberg, National Cancer Institute, Frederick/Bethesda, Md.) by intra-dermal injection on day zero. The tumor cells had been cultivated and prepared according to standard techniques using RPMI media with 10% Fetal Bovine Serum (see for example Current Protocols in Molecular Biology). Beginning on day 5, all animals were treated with the lipid/therapeutic nucleic acid formulation listed in the chart, supra. The formulation was delivered intravenously through the tail vein. 80 µg of pfNEX-TK10 DNA were injected in a total volume of 200 µL. Treatments were administered on days 5, 7, 9, 11 and 13.

Beginning on day 5, all animals were treated with ganciclovir twice daily. 1 mg (~50 mg/kg) were injected intraperitoneally in a total volume of 200 µL PBS. Treatments continued twice daily for 12 days (see, FIGS. 7A and 7B). Mice were monitored for tumor growth.

Figure 8A:
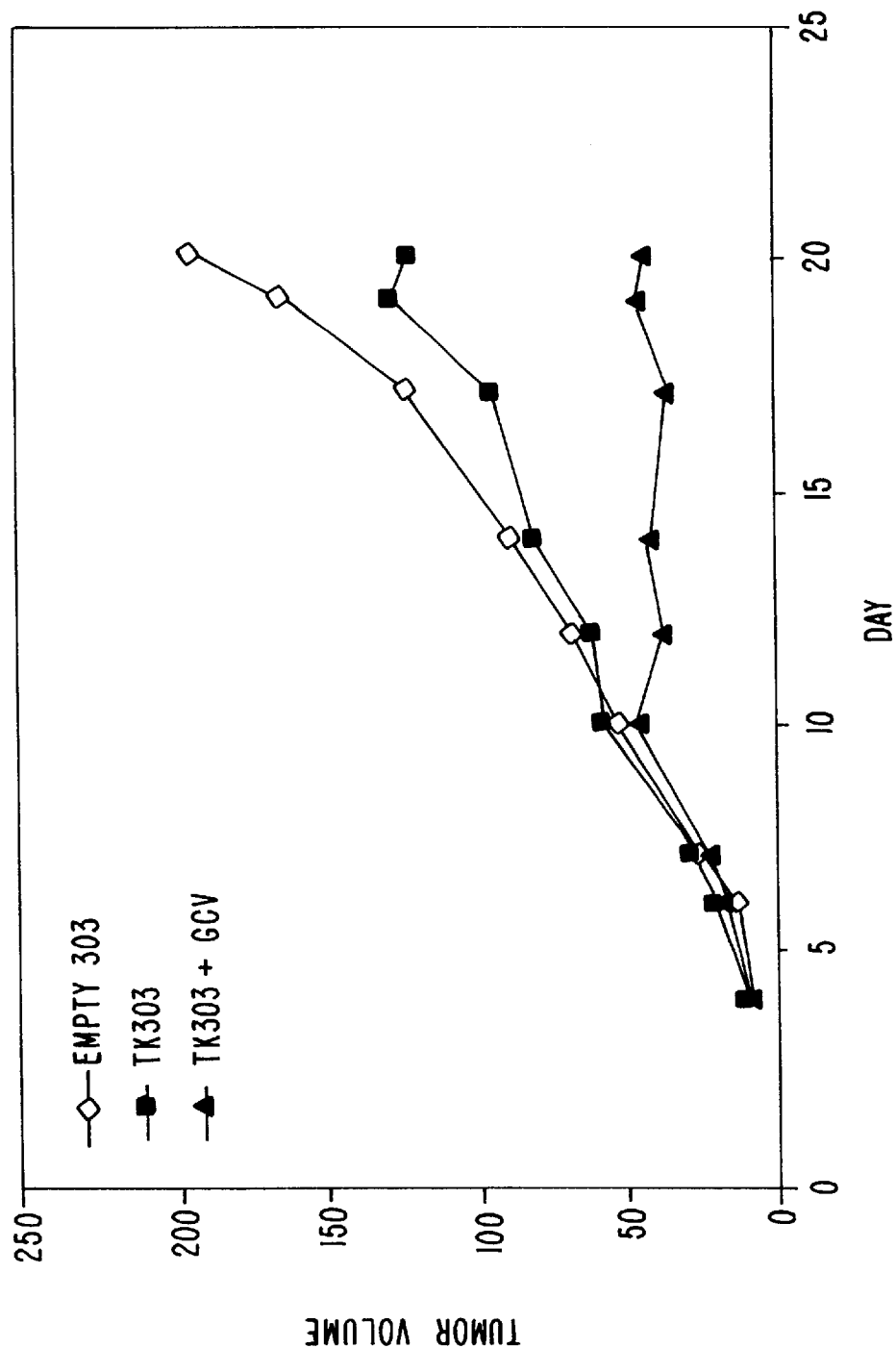
FIG. 8(A) illustrates an assessment of the tumor growth, with the empty formulation showing the largest tumor volume.
Figure 8B:
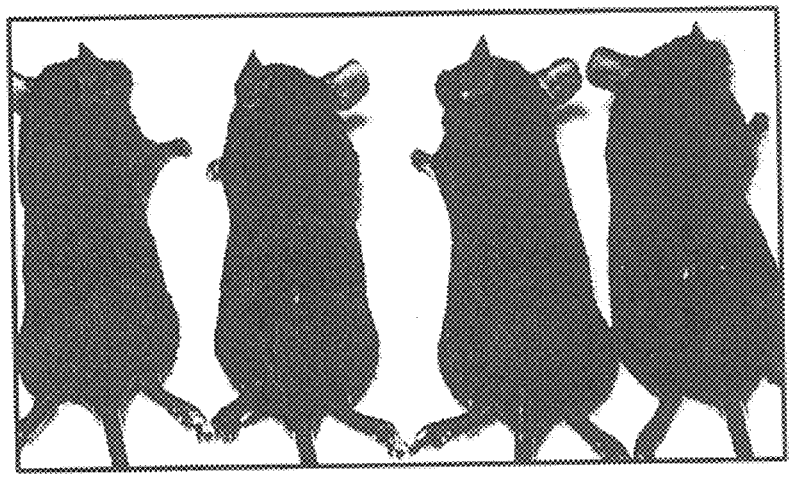
FIG. 8(B) illustrates the efficacy of the suicide gene SPLP of this invention.
Figure 8B:
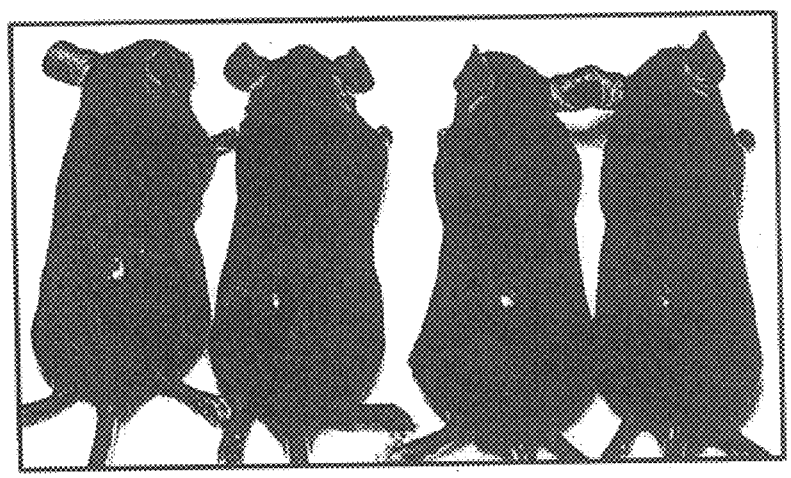

FIG. 8A sets out in more quantitative terms the effect of the treatments. Mice treated with HSV-TK in Formulation 1.1 have greatly reduced tumors compared to control treated mice. Not shown is data of control mice which demonstrates that treatment with empty liposomes and ganciclovir has no effect on tumor reduction. FIG. 8B demonstrates the effect of the treatment on test mice in comparison with control mice at day 16 after tumor inoculation.

L. EXAMPLE 9

1. The Materials

Sphingomyelin and cholesterol were obtained from Northern Lipids (Vancouver, BC). $^{14}$C-cholesteryl hexadecyl ether ($^{14}$C-CHE) was purchased from Amersham (Mississauga, ON). Ethanol, chloroform, methanol, N-(2-hydroxyethyl) piperazine N'-(2-ethanesulphonic acid) (HEPES), hydrogen peroxide and sodium chloride (NaCl) were from VWR Scientific (Mississauga, ON). Ethylenediaminetetraacetic acid (EDTA) was purchased from Sigma (St. Louis, Mo.). Solvable® and Picofluor® scintillation fluids were provided by Canberra Packard Canada (Mississauga, ON). Ganciclovir (GCV) was acquired from Hoffman LaRoche Ltd. (Mississauga, ON). $^3$H-GCV was purchased from Moravek Biochemicals (Brea, Calif.). Female C57BL/6 mice were from Harland Sprague Dawley (Indianapolis, Ind.). The B16 cell line was acquired from the NCI (Frederick, Md.). B16TK cells were produced at Inex according to standard methodology (see, previous Examples).

2. The Preparation of GCV-TCS

Large unilamellar vesicles were prepared according to the method of Hope, et al., *Biochem. Biophys. Acta.* 812:55–65 (1985). 55 mole % sphingomyelin and 45 mole % of cholesterol were dissolved in chloroform with a drop of methanol and approximately 0.035 $\mu$Ci of $^{14}$C-CHE. Lipids were dried down under a stream of nitrogen gas and the resulting lipid film was then placed under high vacuum for at least 3 hrs. A solution of ganciclovir containing $^3$H-GCV was made up in 30% ethanol, 70% HBS (20 mM Hepes, 145 mM NaCl pH 7.45) to 50 or 100 mg/mL depending on the sample size. The lipid to GCV weight ratio was initially 1 to 1. The GCV solution was added to the lipid film. The lipid-GCV solution was heated to 65° C. for 5 min and vortexed well in order to obtain a homogenous solution. The resulting solution was subjected to five freeze-thaw cycles before extrusion through 100 nm filters using an extrusion apparatus (Lipex Biomembranes) heated to 65° C. An extra 1 mL of buffer was added to the solution after the third pass of extrusion. Once extruded, the formulation was dialyzed against HBS overnight with one buffer exchange after one hr of dialysis. The formulation was sized using a quasielastic light scattering (QELS) particle sizer (Nicomp 370). The lipid concentration was determined by scintillation counting of $^{14}$C-CHE label. The GCV concentration was determined by counting $^3$H-GCV and a Bligh Dyer assay.

3. Methods

Groups of four female C57BL/6 mice per time point were injected subcutaneously with 150,000 B16 tumor cells. The tumors were grown for 14 days at which time a single iv dose of free GCV or liposomal GCV was given via the lateral tail vein. This dose, given in a total of 200 $\mu$L, contained approximately 5.6 mg (10 $\mu$moles) lipid and 0.5 mg (1.96 $\mu$moles) GCV resulting in lipid and GCV doses of 300 mg/kg and 25 mg/kg, respectively. Circulating levels of lipid and GCV were determined at 15 min, 1, 8, 24 and 48 hrs for the liposomal GCV groups. Levels of GCV were determined at 15 min and 1 hr for the free GCV groups. At each time point, animals were anesthetized with ketamine/xylazine and blood was collected via cardiac puncture. Blood was put into EDTA coated microtainers and spun at 500 g for 10 min in order to pellet blood cells and obtain plasma. Lipid and GCV levels in the plasma were determined. Lipid and GCV were measured by counting $^{14}$C-CHE and $^3$H-GCV. One hundred or 200 $\mu$L aliquots of plasma were measured on a Beckman LS3801 scintillation counter.

4. Results a. Pharmacokinetics of GCV-TCS in B16 Tumored Mice

Figure 9:
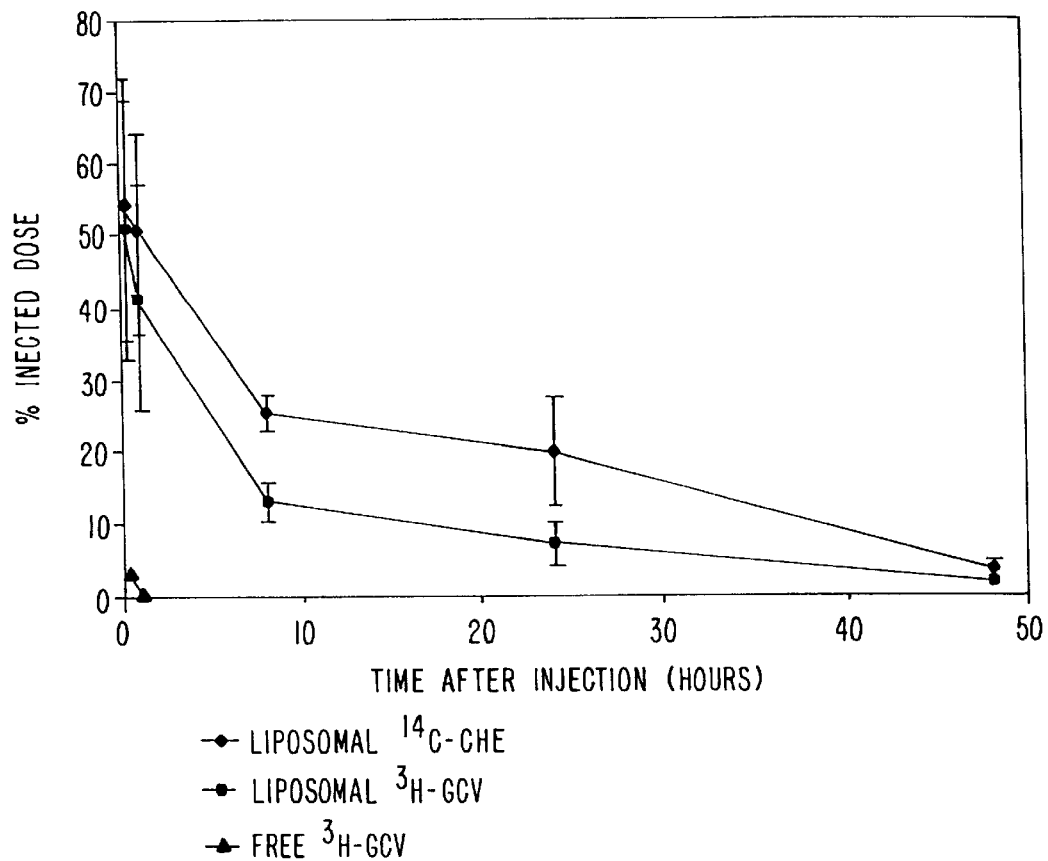
FIG. 9 illustrates serum clearance of liposomal GCV. Plasma was recovered at the indicated time points and assayed for $^3$H-ganciclovir and $^{14}$C-CHE lipid. Results are +/−SEM with n=4.

This example demonstrates plasma clearance rates of free ganciclovir and liposomal ganciclovir. Levels of lipid and GCV were monitored in the plasma by tracing $^{14}$C-CHE and $^3$H-GCV labels. A direct comparison of the pharmacokinetic properties of free and liposomal GCV was made at 15 min and 1 hr. FIG. 9 shows that liposomal encapsulation confers enhanced pharmacokinetics of GCV resulting in an increased circulation lifetime compared to free drug, with a hundred-fold increase in serum drug levels 1 hr after administration. After 1 hr, 41% of the injected dose of liposomal GCV remains in circulation compared with only 0.4% of the free GCV. Animals treated with liposomal GCV have significant amounts of drug (1.5% of the injected dose) in the circulation even after 48 hrs.

b. In Vivo Kinetics of GCV Release

Figure 10:
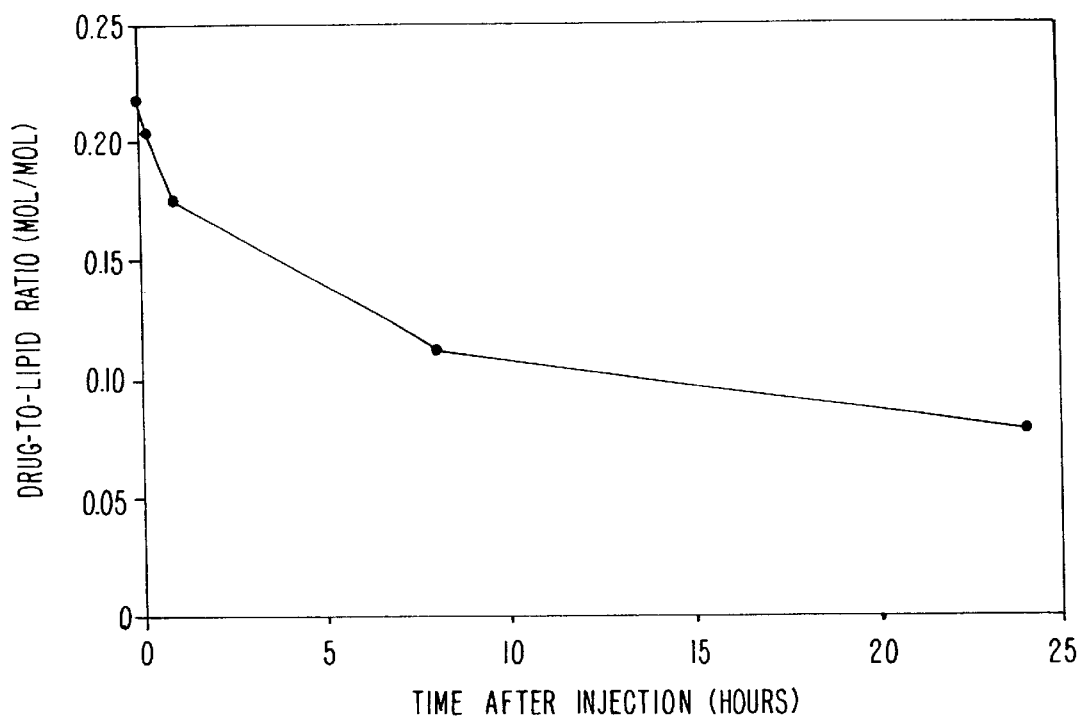
FIG. 10 illustrates in vivo kinetics of GCV release. Plasma was recovered at the indicated time points and assayed for $^3$H-ganciclovir and $^{14}$C-CHE lipid. Retention of ganciclovir in liposomal GCV was evaluated by monitoring the ratio of ganciclovir to lipid.

The bioavailability of lipid-formulated GCV after intravenous administration was determined by comparing lipid and ganciclovir levels in plasma at various times after tail vein injection. The resulting plasma drug-to-lipid ratio was determined. A decrease in the in vivo drug-to-lipid ratio indicates that a portion of the GCV is no longer associated with the liposomal formulation. This free GCV is rapidly cleared from the circulation. The decrease in the relative percent recovery shown in FIG. 10 is suggestive of gradual in vivo drug release.

M. EXAMPLE 10

This example illustrates biodistribution studies

1. Methods

Biodistribution data was collected from those mice that were in the pharmacokinetic studies. Following heart puncture, mice were terminated by cervical dislocation. Tissues were harvested from each animal and weighed. Saline was added to each organ prior to homogenization by either a Polytron homogenizer (livers) or a Fast Prep® machine. Tissues were solubilized in Solvable for 3 to 16 hr at 50° C. The samples were then cooled to room temperature before defoaming and decolourizing with EDTA and hydrogen peroxide respectively. Picofluorscintillation fluid was added to the samples prior to counting on the scintillation counter.

2. Results a. Biodistribution of GCV-TCS in B16 Tumored Mice

Figure 11A:
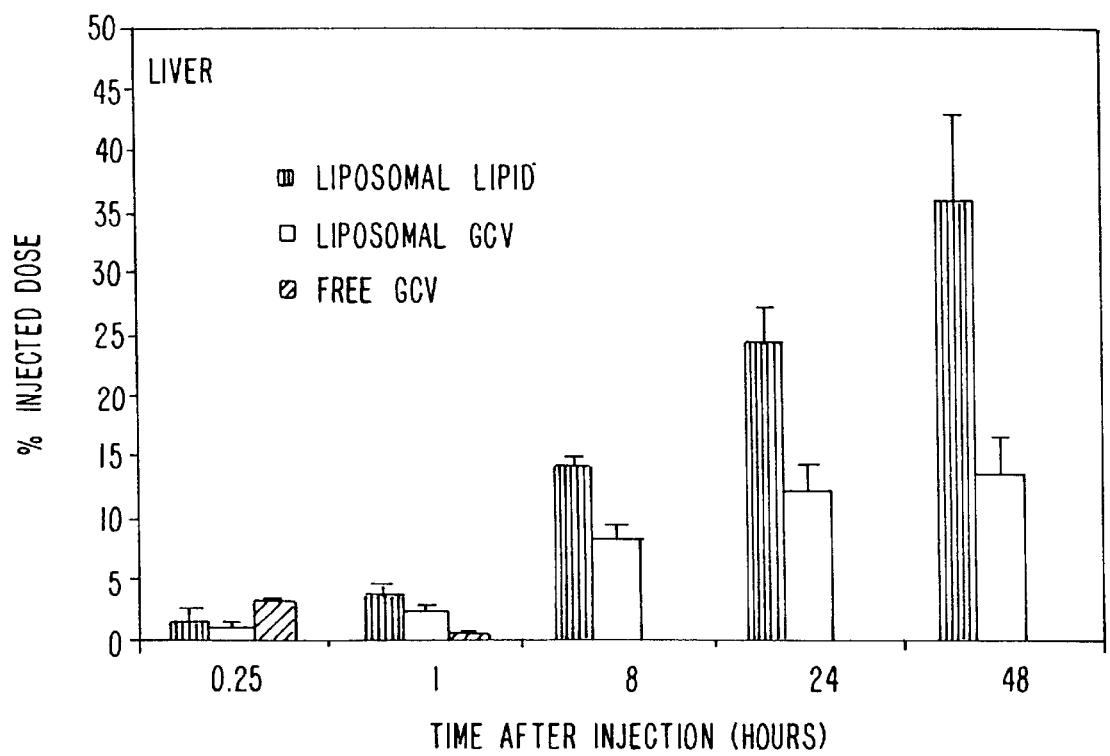
FIGS. 11A, B, C and D illustrate accumulation of liposomal GCV in distal tissue. Organs were recovered at the indicated time points and assayed for $^3$H-ganciclovir and $^{14}$C-CHE lipid. Results are +/−SEM with n=4.

Tumor bearing mice were treated with free or liposomal GCV. Liver, lungs, spleen, and kidneys were analyzed for lipid and ganciclovir content. The major route of elimination for many drugs is the kidney. FIGS. 11A, B, C and D show that free ganciclovir was essentially absent from all of the organs assayed, except for a small amount, 3.5+/−1.8% of the total injected dose, which was found in the kidneys at the 15 minute time point. This finding is consistent with previous studies in humans that found that intravenously administered ganciclovir is rapidly eliminated in the urine. See, Paul, et al., *J. Am. Med. Sci.*, 304:272–277 (1992), and Markham, et al., *Drugs*, 48(3):455–484 (1994). For this reason, free GCV biodistribution data were not collected beyond 1 hr. A similar amount of free GCV, 3.1+/−0.1 % of the initial injected dose, was found in the liver 15 minutes after administration, but this represents a much lower relative dose because of the large size of this organ.

The biodistribution of liposomal GCV was considerably different from that of the free drug. Liposomal formulations are typically cleared from circulation by the organs of the reticuloendothelial system (RES), the spleen and liver. See, Lim, et al., *J. Pharmacol. Exp. Ther.*, 281(1):566–573 (1997), Gregoridis, et al., *Drugs*, 45(1):15–28 (1993) and Cullis, et al., "Liposomes as Pharmaceuticals," *Liposomes* (Ostro, M. (ed.), Marcel Dekker: New York, pp. 39–72 (1987)). FIG. 11A illustrates a significant increase in liposomal GCV accumulation in the liver over time, with a maximum accumulation of 13.6+/−3.1% of the total injected dose 48 hrs after administration. The liver also accumulates a similar amount of lipid at early time points. However, at 24 and 48 hrs, a significantly greater percentage of the lipid dose accumulates in the liver. This may represent an accumulation of empty liposomal particles or a remodeling of lipid components with concomitant uptake in the form of lipoproteins.

Figure 11B:
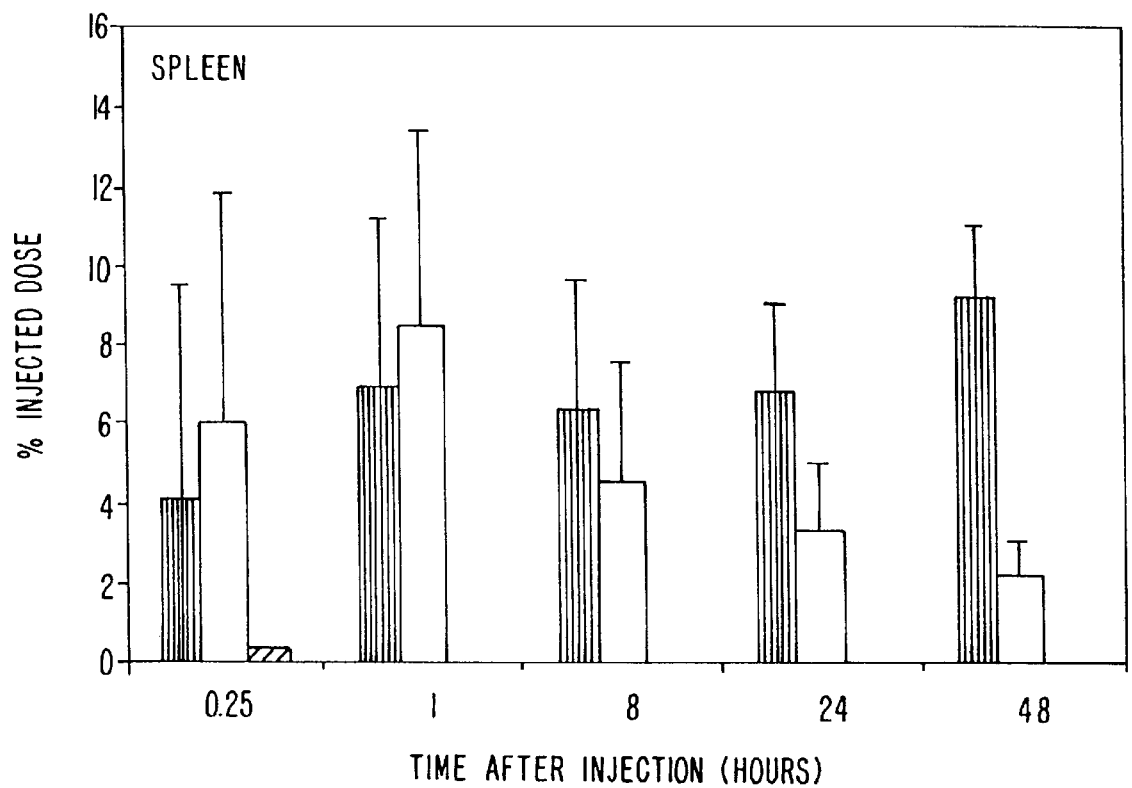
FIG. 11B, spleen.
Figure 11C:
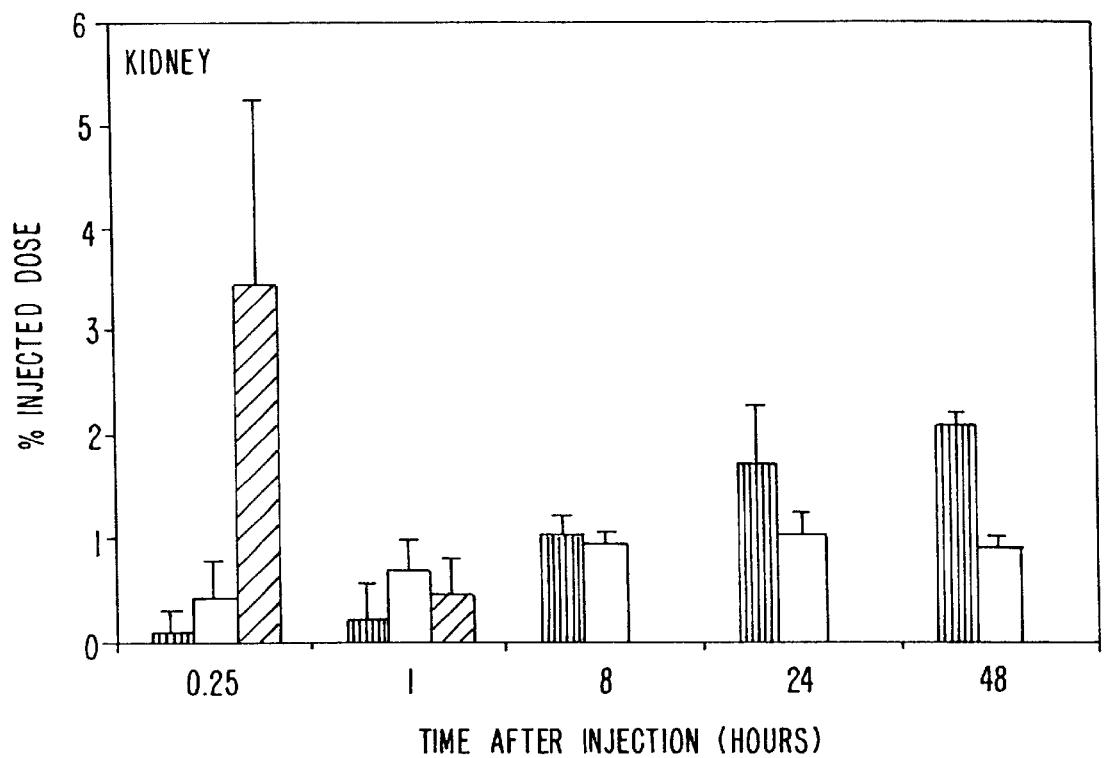
FIG. 11C, lung.
Figure 11D:
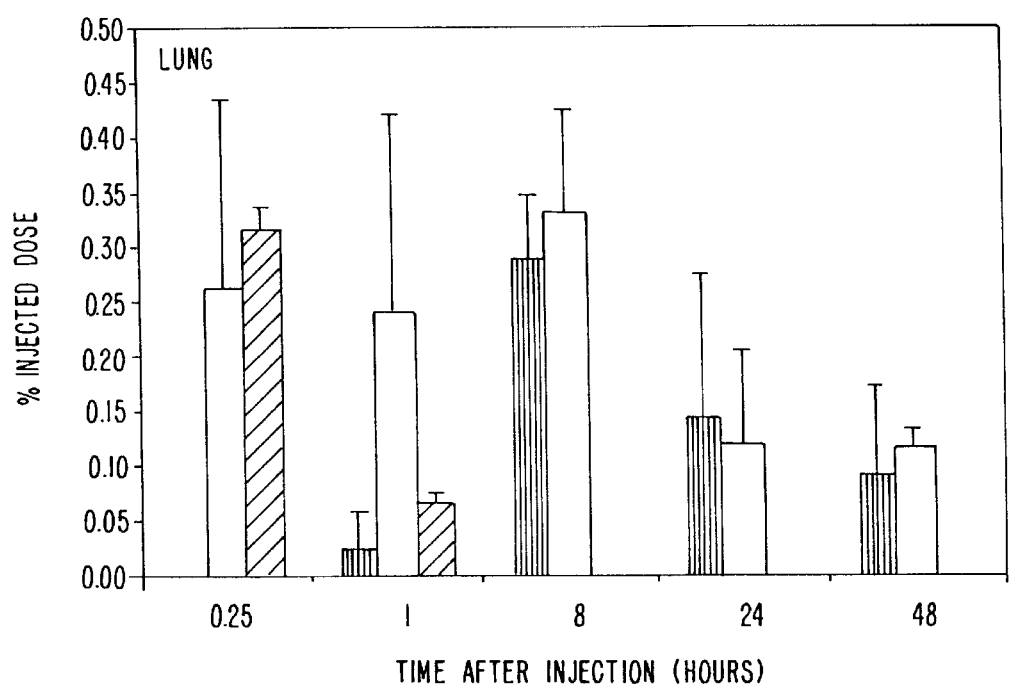
FIG. 11D, kidney.

The kinetics of liposomal GCV uptake in the spleen differ significantly from the situation in liver. FIG. 11B illustrates that the spleen rapidly accumulates as much as 8.5+/−4.8% of the total injected liposomal GCV dose with a peak at 1 hr. At this time, only 0.04+/−0.02% of the free drug remains in the spleen. This difference in kinetics suggests a mechanistic difference, possibly involving uptake and redirection of liposomes by homing macrophages. Intravenous administration of liposomal GCV resulted in a minimal accumulation of GCV in the kidney (see, FIG. 11D) and lung (see, FIG. 11C) persisting from 1 to 48 hr. This maintenance of GCV in the kidney may be a reflection of the rapid clearance of GCV from the blood as it becomes bioavailable. Minimal accumulation of free GCV or liposomal GCV over the entire time course (less than 0.35% of the total injected dose) was observed in the lung. Liposomes of this size (100 nm) typically do not accumulate in the lung.

In summary, the free GCV accumulated to the largest extent in the kidney, whereas the liposomal GCV accumulated in the spleen and liver.

b. Tumor Accumulation of GCV-TCS

Figure 12:
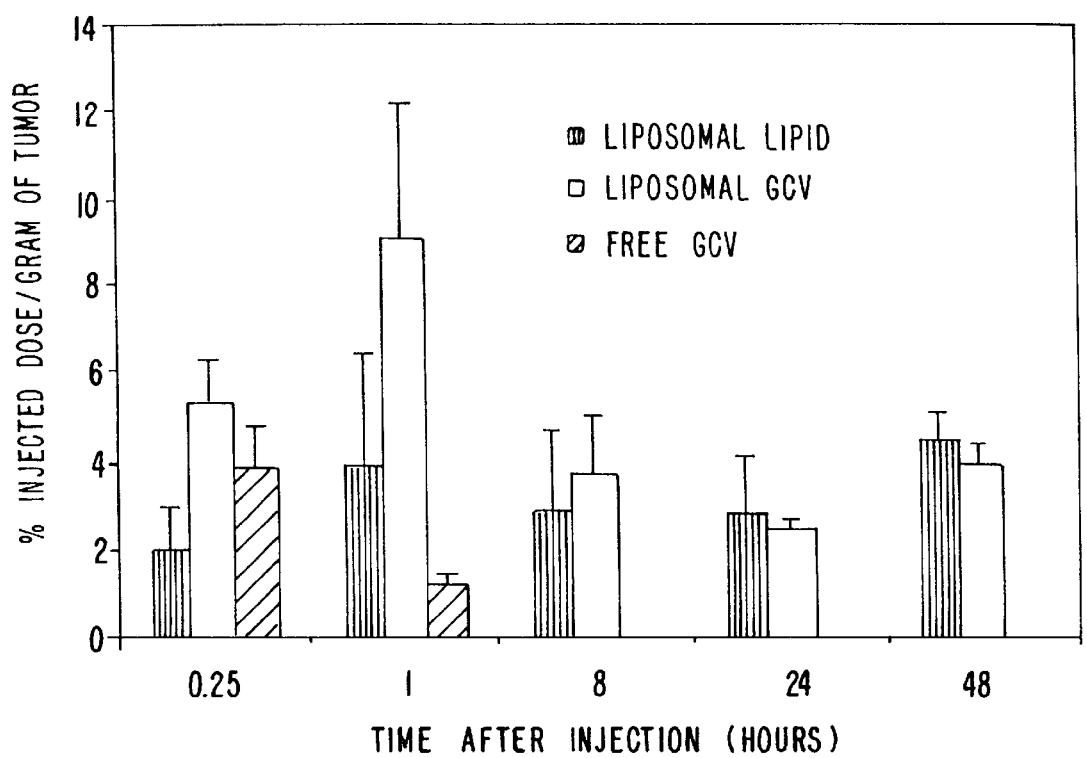
FIG. 12 illustrates tumor accumulation of liposomal GCV. Tumors were recovered at the indicated time points and assayed for $^3$H-ganciclovir and $^{14}$C-CHE lipid. Results are +/−SEM with n=4.

Tumor bearing mice were treated intravenously with 25 mg/kg of free or liposomal GCV. Lipid and GCV were quantified using $^{14}$C-CHE and $^{3}$H-GCV labels. FIG. 12 illustrates that the accumulations of both free and encapsulated GCV in the tumor are comparable at early time points, but that encapsulated GCV has extended bioavailability at the disease site. Free ganciclovir is rapidly cleared from the tumor, with only 1.1+/−0.1 % of the total injected dose per gram of tumor detected at 1 hr. Liposomal formulation results in maintenance of GCV in the tumor over the course of the experiment. Forty-eight hrs after treatment, there is still 3.9+/−0.5% of the total injected dose per gram of tumor tissue. The high drug-to-lipid ratio at the tumor suggests that some of the GCV that is no longer associated with lipid is accumulating there. The mechanism of action of GCV involves inhibition of DNA polymerase and termination of DNA synthesis via chain termination (see, Paul, et al., *J. Am. Med. Sci.*, 304:272–277 (1992), Markham, et al., *Drugs*, 48(3):455–484 (1994) and Oja, et al., BBA, 1281:31–37 (1996)). Since not all tumor cells can be expected to undergo DNA synthesis during the short time period in which free GCV is accumulating, and because the intracellular stability of GCV, GCV-MP and GCV-TP is not well understood, it is believed that there are significant benefits associated with long-term, continuous GCV exposure. Quite importantly, the liposomal formulations described herein have extended bioavailability at the disease site compared with the free drug.

N. EXAMPLE 11

This example illustrates efficacy studies.

1. Methods

Groups of 4 or 5 female C57BL/6 mice were injected intradermally with B16 cells stably transfected with HSV-TK. Once tumors were measurable (day 5), the mice were injected intravenously with liposomal GCV (25 mg/kg GCV). Injections were continued every other day for 6 injections. Tumor measurements were typically taken every other day.

2. Results a. In Vivo Efficacy of GCV-TCS in the B16TK Model

Figure 13:
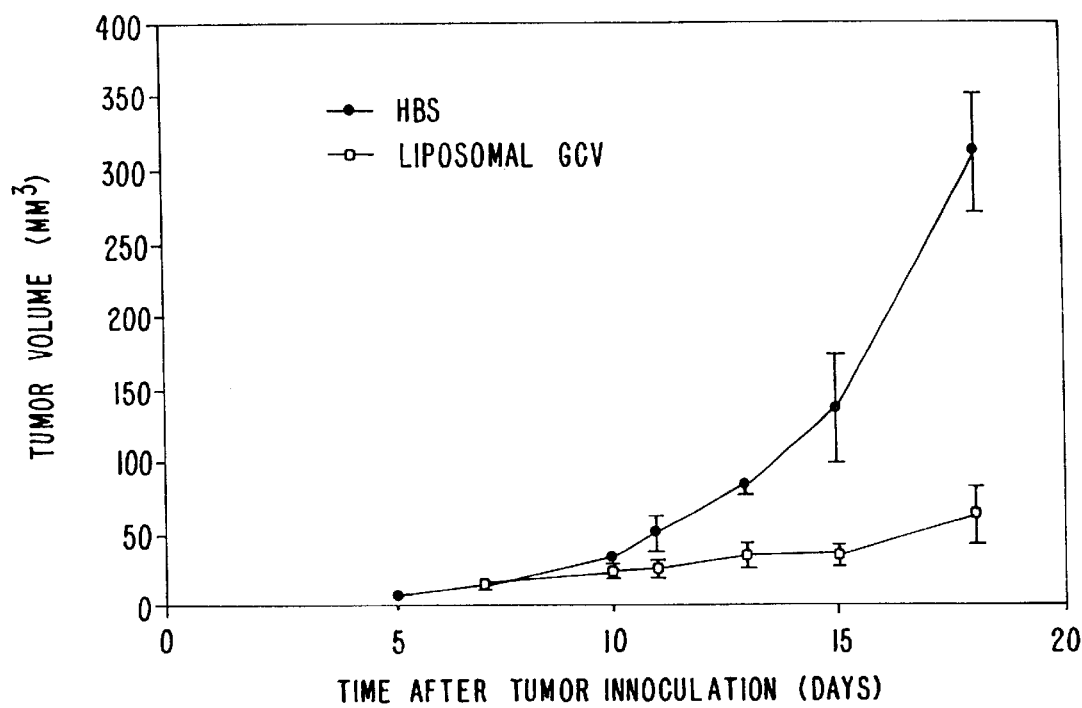
FIG. 13 illustrates efficacy of liposomal ganciclovir in the B16TK tumor model. Female C57BL/6 mice were seeded subcutaneously in the hind flank with 150,000 B16 murine melanoma cells stably transfected with HSV-TK. Five days later, tumor measurement began. Starting on day five, mice were treated with liposomal or free GCV (25 mg/kg ganciclovir) or HBS (Hepes Buffered Saline) every other day for a total of six injections. Measurements at day 18 indicate that tumors in the control mice are 5-fold larger than FIG. 14A illustrates pINEX L018 plasmid contruct description and map.

To test whether the lipid-formulated ganciclovir retains its biological activity, an in vivo efficacy experiment was performed. Mice were seeded with B16 melanoma cells stably transfected with HSV-TK. FIG. 13 illustrates that the treatment of mice with liposomal GCV significantly inhibits the growth of B16-TK melanoma. Measurements on day 18 indicated that tumors in the control HBS-treated mice were fivefold larger than those in the treated groups. These results confirm that the formulation process did not compromise the structural integrity of GCV, and provide additional evidence of the bioavailability of the drug.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A method of sensitizing a cell to an anti-tumor compound, said method comprising:
    a) transfecting a cell with a vector comprising a polynucleotide sequence encoding a prodrug activating enzyme that promotes the processing of a non-lipid derivatized prodrug into said anti-tumor compound; and
    b) delivering to said cell said non-lipid derivatized prodrug in a lipid formulation;
wherein said cell is more sensitive to said anti-tumor compound than said non-lipid derivatized prodrug.

2. The method of claim 1 wherein said vector is in a lipid formulation.

3. The method of claim 2 wherein said vector is in a lipid encapsulated formulation.

4. The method of claim 3 wherein said vector is fully encapsulated in said lipid encapsulated formulation.

5. The method of claim 2 wherein said vector is naked DNA.

6. The method of claim 2 wherein said lipid formulation comprises a cationic lipid, and a compound which delays clearance of said lipid formulation from the circulation.

7. The method of claim 6 wherein said lipid formulation comprises DODAC, and a polyamide oligomer linked lipid.

8. The method of claim 1 wherein said vector is a cationic lipid-vector aggregate.

9. The method of claim 1 wherein said vector is a modified adenovirus or modified retrovirus.

10. The method of claim 1 wherein said lipid formulation comprises sphingomyelin and cholesterol.

11. The method of claim 1 wherein said lipid formulation comprises a cationic lipid and said vector is in a lipid formulation comprising a cationic lipid.

12. The method of claim 1 wherein the cell is in an organism and the vector is delivered systemically.

13. The method of claim 12 or 1 wherein the organism is a mammal.

14. The method of claim 1 wherein the cell is in an organism and the vector is delivered regionally or locally.

15. The method of claim 1 wherein said enzyme is a member selected from the group consisting of herpes simplex virus thymidine kinase, cytosine deaminase, xanthine-guaninephosphoribosyl transferase, purine nucleoside phosphorylase, cytochrome P450 2B1 and their analogs.

16. The method of claim 1 wherein said prodrug is selected from the group consisting of ganciclovir, acyclovir, bromovinyldeoxyuridine, 5-fluorocytosine, 6-thioxanthine, MeP-dr and cyclophosphamide.

17. The method of claim 16 wherein said prodrug is ganciclovir and said lipid formulation comprises sphingomyelin.

18. A method of sensitizing a cell to an anti-tumor compound, said method comprising:

a) delivering to a cell an enzyme that promotes the processing of a non-lipid derivatized prodrug into said anti-tumor compound; and b) delivering to the cell said non-lipid derivatized prodrug in a lipid formulation;

wherein said cell is more sensitive to said anti-tumor compound than said non-lipid derivatized prodrug.

19. A kit for the treatment of a human tumor, said kit comprising:

a) a vector comprising a polynucleotide sequence encoding a prodrug activating enzyme in a lipid formulation; and b) a lipid formulation comprising a non-lipid derivatized prodrug that can be activated by said enzyme.

20. A composition, said composition comprising a) a non-lipid derivatized prodrug in a lipid formulation;

b) a vector comprising a polynucleotide encoding a prodrug activating enzyme; and c) a pharmaceutically acceptable carrier.

21. The composition of claim 20, wherein said vector is in a lipid formulation.

22. The composition of claim 21, wherein the lipid formulations are different.

* * * * *